United States Patent
Liang et al.

(10) Patent No.: US 7,320,871 B2
(45) Date of Patent: Jan. 22, 2008

(54) HUMAN PROSTAGLANDIN FP RECEPTOR VARIANTS AND METHODS OF USING SAME

(75) Inventors: Yanbin Liang, Irvine, CA (US); David F. Woodward, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 390 days.

(21) Appl. No.: 10/620,289

(22) Filed: Jul. 14, 2003

(65) Prior Publication Data

US 2006/0105346 A1 May 18, 2006

(51) Int. Cl.
C07K 14/705 (2006.01)
G01N 33/566 (2006.01)

(52) U.S. Cl. ................ 435/7.2; 435/7.21; 435/69.1; 530/350

(58) Field of Classification Search ............... None
See application file for complete search history.

(56) References Cited

U.S. PATENT DOCUMENTS

| | | | |
|---|---|---|---|
| 5,869,281 A | 2/1999 | Abramovitz et al. | 435/69.1 |
| 6,329,426 B1 | 12/2001 | Ueno | 514/530 |
| 6,416,972 B1 | 7/2002 | Lake et al. | 435/69.1 |
| 6,492,417 B1 | 12/2002 | Sharif et al. | 514/530 |
| 6,511,999 B2 | 1/2003 | Burk et al. | 514/374 |
| 2004/0082013 A1 | 4/2004 | Regan | |

FOREIGN PATENT DOCUMENTS

| | | |
|---|---|---|
| WO | WO 00/29614 | 5/2000 |
| WO | WO 03/070902 | 8/2003 |

OTHER PUBLICATIONS

Abramovitz et al., "Cloning and expression of a cDNA for the human prostanoid FP receptor," *J. Biol. Chem.* 269:2632-2636 (1994).
Anderson et al., "Prostaglandin $F_{2\alpha}$ receptor in the corpus luteum: Recent information on the gene, messenger ribonucleic acid, and protein," *Biology of Reproduction* 64:1041-1047 (2001).
Anderson et al., "Prostaglandin moieties that determine receptor binding specificity in the bovine corpus luteum," *J. Reprod. Fertil.* 116:133-141 (1999).
Betz et al., "Genomic structure, 5' flanking sequences, and precise localization in 1P31.1 of the human prostaglandin F receptor gene," *Biochem. Biophys. Res. Commun.* 254:413-416 (1999).
Bhattacharya et al., "Nuclear prostaglandin receptors," *Gene Ther. Mol. Biol.* 4:323-338 (1999).
Boiti et al., "Nitric oxide synthase activity and progesterone release by isolated corpora lutea of rabbits in the early and mid-luteal phases of pseudopregnancy are modulated differently by prostaglandin E-2 and prostaglandin F-2alpha via adenylate cyclase and phospholipase C," *J. Endocrinol.* 164:179-186 (2000).
Carrasco et al., "Activation of the prostaglandin FP receptor in human granulosa cells," *J. Reprod. Fertil.* 111:309-317 (1997).
Chen et al., "Prostaglandin F2alpha stimulates the Raf/MEK1/mitogen-activated protein kinase signaling cascade in bovine luteal cells," *Endocrinology* 139:3876-3885 (1998).
Davis et al., "Prostaglandin F2 alpha stimulates phosphatidylinositol 4,5-bisphosphate hydrolysis and mobilizes intracellular Ca2+ in bovine luteal cells," *Proc. Natl. Acad. Sci. USA* 84:3728-3732 (1987).
Duncan et al., "Chromosomal localization of the human prostanoid receptor gene family," *Genomics* 25:740-742 (1995).
Ezashi et al., "Genomic organization and characterization of the gene encoding bovine prostaglandin F2alpha receptor," *Gene* 190:271-278 (1997).
Fu et al., "Peroxisome proliferator-activated receptor gamma inhibits transforming growth factor beta-induced connective tissue growth factor expression in human aortic smooth muscle cells by interfering with Smad3," *J. Biol. Chem.* 276:45888-45894 (2001).
Fujino et al., "Delayed reversal of shape change in cells expressing $FP_{(B)}$ prostanoid receptors. Possible role of receptor resensitization," *J. Biol. Chem.* 275:29907-29914 (2000).
Graves et al., "Cloning of a receptor for prostaglandin F2 alpha from the ovine corpus luteum," *Endocrinology* 136:3430-3436 (1995).
Griffin et al., "FP prostaglandin receptors mediating inositol phosphates generation and calcium mobilization in Swiss 3T3 cells: A pharmacological study," *J. Pharmacol. Exp. Ther.* 281:845-854 (1997).
Gusovsky, "Prostaglandin receptors in NIH 3T3 cells: Coupling of one receptor to adenylate cyclase and of a second receptor to phospholipase C," *Mol. Pharmacol.* 40:633-638 (1991).
Hasumoto et al., "Characterization of the mouse prostaglandin F receptor gene: A transgenic mouse study of a regulatory region that controls its expression in the stomach and kidney but not in the ovary," *Genes Cells* 2:571-580 (1997).
Ishikawa et al., "Mapping of the genes encoding mouse prostaglandin D, E, and F and prostacyclin receptors," *Genomics* 32:285-288 (1996).
Juengel et al., "Regulation of steady-state concentrations of messenger ribonucleic acid encoding prostaglandin F2 alpha receptor in ovine corpus luteum," *Biol. Reprod.* 54:1096-1102 (1996).

(Continued)

Primary Examiner—John Ulm
(74) Attorney, Agent, or Firm—Joel B. German; Dean G. Stathakis; Martin A. Voet

(57) ABSTRACT

The invention provides an isolated polypeptide containing the amino acid sequence of SEQ ID NO: 17, 18, 19, 20, 21, 22, 23, 24, or 25. The invention also provides an isolated polypeptide containing an amino acid sequence having at least 50% amino acid identity with SEQ ID NO: 14 and an amino acid sequence of SEQ ID NO: 17, 18, 19, 20, 21, 22, 23, 24, or 25, or a conservative variant thereof. The invention further provides an isolated polypeptide containing the amino acid sequence of SEQ ID NO: 2, 4, 6, 8, 10, or 12. The invention also provides a method for identifying a compound that modulates a FP receptor variant by contacting an isolated FP receptor variant or a FP receptor variant overexpressed in a genetically engineered cell with a compound and determining the level of an indicator which correlates with modulation of a FP receptor variant, where an alteration in the level of the indicator as compared to a control level indicates that the compound is a compound that modulates the FP receptor variant.

10 Claims, 10 Drawing Sheets

OTHER PUBLICATIONS

Kiriyama et al., "Ligand binding specificities of the eight types and subtypes of the mouse prostanoid receptors expressed in Chinese hamster ovary cells," *Br. J. Pharmacol.* 122:217-224 (1997).

Kitanaka et al., "Cloning and expression of a cDNA for rat prostaglandin F2 alpha receptor," *Prostaglandins* 48:31-41 (1994).

Lake et al., "Cloning of the rat and human prostaglandin F2 alpha receptors and the expression of the rat prostaglandin F2 alpha receptor," *FEBS Lett.* 355:317-325 (1994).

Liang et al., "Comparison of PGF2α, Bimatoprost (prostamide) and butaprost (EP2 agonist) of Cyr61 and CTGF gene expression," *J. Biol. Chem.* 278:27267-27277 (2003).

Liu et al., "PLD activation in Chinese hamster ovary (CHO) cells transfected with PGF2 alpha receptor cDNA," *Prostaglandins* 51:233-248 (1996).

Narumiya and FitzGerald, "Genetic and pharmacological analysis of prostanoid receptor function," *J. Clin. Invest.* 108:25-30 (2001).

Niswender et al., "Mechanisms controlling the function and life span of the corpus luteum," *Physiol. Rev.* 80:1-29 (2000).

Ogawa et al., "Structural organization and chromosomal assignment of the human prostacyclin receptor gene," *Genomics* 27:142-148 (1995).

Pierce and Regan, "Prostanoid receptor heterogeneity through alternative mRNA splicing," *Life Sciences* 62:1479-1483 (1998).

Pierce et al., "Activation of FP prostanoid receptor isoforms leads to Rho-mediated changes in cell morphology and in the cell cytoskeleton," *J. Biol. Chem.* 274:35944-35949 (1999).

Pierce et al., "Cloning of a carboxyl-terminal isoform of the prostanoid FP receptor," *J. Biol. Chem.* 272:883-887 (1997).

Sakamoto et al., "Expression of mRNA encoding the prostaglandin F2 alpha receptor in bovine corpora lutea throughout the oestrous cycle and pregnancy," *J. Reprod. Fertil.* 103:99-105 (1995).

Sakamoto et al., "Molecular cloning and expression of a cDNA of the bovine prostaglandin F2 alpha receptor," *J. Biol. Chem.* 269:3881-3886 (1994).

Sakamoto et al., "Prostaglandin F2 alpha receptor," *J. Lipid Mediat. Cell Signal* 12:405-411 (1995).

Stjernschantz et al., "Microvascular effects of selective prostaglandin analogues in the eye with special reference to latanoprost and glaucoma treatment," *Prog. Retin. Eye Res.* 19:459-496 (2000).

Sugimoto et al., "Cloning and expression of a cDNA for mouse prostaglandin F receptor," *J. Biol. Chem.* 269:1356-1360 (1994).

Susanna et al., "Current status of prostaglandin theory: Latanoprost and unoprostone," *Surv. Ophthalmol.* 47:S97-104 (2002).

Taketo et al., "Mapping of the genes encoding mouse thromboxane A2 receptor and prostaglandin E-receptor subtypes EP2 and EP3," *Genomics* 19:585-588 (1994).

Tsai et al., "Distinct mechanisms regulate induction of messenger ribonucleic acid for prostaglandin (PG) G/H synthase-2, PGE (EP3) receptor, and PGF2 alpha receptor in bovine preovulatory follicles," *Endocrinology* 137:3348-3355 (1996).

Tsai et al., "Regulation of prostaglandin F2 alpha and E receptor mRNA by prostaglandin F2 alpha in ovine corpora lutea," *J. Reprod. Fertil.* 114:69-75 (1998).

Tsai and Wiltbank, "Prostaglandin F2 alpha regulates distinct physiological changes in early and mid-cycle bovine corpora lutea," *Biol. Reprod.* 58:346-352 (1998).

Uemura et al., "Identification of a new enhancer in the promoter region of human TR3 orphan receptor gene. A member of steroid receptor superfamily," *J. Biol. Chem.* 270:5427-5433 (1995).

Weinreb et al., "Effects of prostaglandins on the aqueous humor outflow pathways," *Surv. Ophthalmol.* 47:S53-64 (2002).

Wiltbank et al., "Hormonal regulation of free intracellular calcium concentrations in small and large ovine luteal cells," *Biol. Reprod.* 41:771-778 (1989).

Woodward et al., "The molecular biology and ocular distribution of prostanoid receptors," *Surv. Ophthalmol.* 41:S15-21 (1997).

Woodward and Lawrence, "Identification of a single (FP) receptor associated with prostanoid-induced Ca2+ signals in Swiss 3T3 cells," *Biochem. Pharmacol.* 47:1567-1574 (1994).

Genbank Accession No. AAB36298.
Genbank Accession No. AAL36977.
Genbank Accession No. AB083784.
Genbank Accession No. AB083785.
Genbank Accession No. AB083786.
Genbank Accession No. AB083787.
Genbank Accession No. AB083788.
Genbank Accession No. AL136324.6.
Genbank Accession No. BAA20871.
Genbank Accession No. BG196146.
Genbank Accession No. BG199710.
Genbank Accession No. BG208551.
Genbank Accession No. BG209077.
Genbank Accession No. BG218035.
Genbank Accession No. BG220560.
Genbank Accession No. NM_000959.
Genbank Accession No. NP_037247.
Genbank Accession No. P43117.
Genbank Accession No. Q28905.

Breyer et al., "Prostanoid receptors: Subtypes and signaling," *Annu. Rev. Pharmacol. Toxicol.* 41:661-690 (2001).

Sakamoto et al., "Cloning and characterization of the novel isoforms for $PGF_{2\alpha}$ receptor in the bovine corpus luteum," *DNA Sequence* 13(5):307-311 (2002).

Vielhauer et al., "Cloning and localization of $hFP_s$: a six-transmembrane mRNA splice variant of the human FP prostanoid receptor," *Archives of Biochem. Biophys.* 421:175-185 (2004).

FP Receptor Variant VAR-1

```
atgtccatga acaattccaa acagctagtg tctcctgcag ctgcgcttct ttcaaacaca 61
acctgccaga cggaaaaccg gctttccgta ttttttcag taatcttcat gacagtggga 121
atcttgtcaa acagccttgc catcgccatt ctcatgaagg catatcagag atttagacag 181
aagtccaagg catcgtttct gcttttggcc agcggcctgg taatcactga tttctttggc 241
catctcatca atggagccat agcagtattt gtatatgctt ctgataaaga atggatccgc 301
tttgaccaat caaatgtcct ttgcagtatt tttggtatct gcatggtgtt ttctggtctg 361
tgcccacttc ttctaggcag tgtgatggcc attgagcggt gtattggagt cacaaaacca 421
atatttcatt ctacgaaaat tacatccaaa catgtgaaaa tgatgttaag tggtgtgtgc 481
ttgtttgctg ttttcatagc tttgctgccc atccttggac atcgagacta taaaattcag 541
gcgtcgagga cctggtgttt ctacaacaca gaagacatca aagactggga agatagattt 601
tatcttctac ttttttcttt tctggggctc ttagcccttg gtgtttcatt gttgtgcaat 661
gcaatcacag gaattacact tttaagagtt aaatttaaaa gtcagcagca cagacaaggc 721
agatctcatc atttggaaat ggtaatccag ctcctggcga taatgtgtgt ctcctgtatt 781
tgttggagcc catttctggg atacagaata attttgaatg ggaaagagaa atataaagta 841
tatgaagagc aaagtgattt cttacatagg ttacaatggc caacattgga aTAAatggaa 901
atcattctct ggaaacctgt gaaacaacac tttttgctct ccgaatggca acatggaatc 961
aaatcttaga tccttgggta tatattcttc tacgaaaggc tgtccttaag aatctctata 1021
agcttgccag tcaatgctgt ggagtgcatg tcatcagctt acatatttgg gagcttagtt 1081
ccattaaaaa ttccttaaag gttgctgcta tttctgagtc accagttgca gagaaatcag 1141
caagcaccta g
```

FIGURE 1

FP Receptor Variant VAR-2

```
atgtccatga acaattccaa acagctagtg tctcctgcag ctgcgcttct ttcaaacaca  61
acctgccaga cggaaaaccg gctttccgta ttttttcag  taatcttcat gacagtggga 121
atcttgtcaa acagccttgc catcgccatt ctcatgaagg catatcagag atttagacag 181
aagtccaagg catcgtttct gcttttggcc agcggcctgg taatcactga tttctttggc 241
catctcatca atggagccat agcagtattt gtatatgctt ctgataaaga atggatccgc 301
tttgaccaat caaatgtcct tgcagtatt  tttggtatct gcatggtgtt ttctggtctg 361
tgcccacttc ttctaggcag tgtgatggcc attgagcggt gtattggagt cacaaaacca 421
atatttcatt ctacgaaaat tacatccaaa catgtgaaaa tgatgttaag tggtgtgtgc 481
ttgtttgctg ttttcatagc tttgctgccc atccttggac atcgagacta taaaattcag 541
gcgtcgagga cctggtgttt ctacaacaca gaagacatca aagactggga agatagattt 601
tatcttctac ttttttcttt tctggggctc ttagcccttg gtgtttcatt gttgtgcaat 661
gcaatcacag gaattacact tttaagagtt aaatttaaaa gtcagcagca cagacaaggc 721
agatctcatc atttggaaat ggtaatccag ctcctggcga taatgtgtgt ctcctgtatt 781
tgttggagcc catttctgaa aatagaagga aaaataaaag tcacaTGAgt gaaggagaaa 841
cagaacgcaa gggtgaaaac aaggcaatta gggcagcaga aagctggtgg tatgagggtg 901
aagagaggca ctctcatgtt ttgggaactc tgttggaaag gttacaatgg ccaacattgg 961
aataaatgga atcattctc  tggaaacctg tgaaacaaca cttttgctc  tccgaatggc 1021
aacatggaat caaatcttag atccttgggt atatattctt ctacgaaagg ctgtccttaa 1081
gaatctctat aagcttgcca gtcaatgctg tggagtgcat gtcatcagct tacatatttg 1141
ggagcttagt tccattaaaa attccttaaa ggttgctgct atttctgagt caccagttgc 1221
agagaaatca gcaagcacct ag
```

FIGURE 2

FP Receptor Variant VAR-3

```
atgtccatga acaattccaa acagctagtg tctcctgcag ctgcgcttct ttcaaacaca  61
acctgccaga cggaaaaccg gctttccgta ttttttttcag taatcttcat gacagtggga 121
atcttgtcaa acagccttgc catcgccatt ctcatgaagg catatcagag atttagacag 181
aagtccaagg catcgtttct gcttttggcc agcggcctgg taatcactga tttctttggc 241
catctcatca atggagccat agcagtattt gtatatgctt ctgataaaga atggatccgc 301
tttgaccaat caaatgtcct ttgcagtatt tttggtatct gcatggtgtt ttctggtctg 361
tgcccacttc ttctaggcag tgtgatggcc attgagcggt gtattggagt cacaaaacca 421
atatttcatt ctacgaaaat tacatccaaa catgtgaaaa tgatgttaag tggtgtgtgc 481
ttgtttgctg ttttcatagc tttgctgccc atccttggac atcgagacta taaaattcag 541
gcgtcgagga cctggtgttt ctacaacaca gaagacatca aagactggga agatagattt 601
tatcttctac ttttttcttt tctggggctc ttagcccttg gtgtttcatt gttgtgcaat 661
gcaatcacag gaattacact tttaagagtt aaatttaaaa gtcagcagca cagacaaggc 721
agatctcatc atttggaaat ggtaatccag ctcctggcga taatgtgtgt ctcctgtatt 781
tgttggagcc catttctggg atacagaata attttgaatg ggaaagagaa atataaagta 841
tatgaagagc aaagtgattt cttacataga aaaTAGaagg aaaaataaaa gtcacatgag 901
tgaaggagaa acagaacgca agggtgaaaa caaggcaatt agggcagcag aaagctggtg 961
gtatgagggt gaagagaggc actctcatgt tttgggaact ctgttggaaa ggttacaatg 1021
gccaacattg gaataaatgg aaatcattct ctggaaacct gtgaaacaac acttttttgct 1081
ctccgaatgg caacatggaa tcaaatctta gatccttggg tatatattct tctacgaaag 1141
gctgtcctta agaatctcta taagcttgcc agtcaatgct gtggagtgca tgtcatcagc 1221
ttacatattt gggagcttag ttccattaaa aattccttaa aggttgctgc tatttctgag 1281
tcaccagttg cagagaaatc agcaagcacc tag
```

FIGURE 3

FP Receptor Variant VAR-4

```
atgtccatga acaattccaa acagctagtg tctcctgcag ctgcgcttct ttcaaacaca   61
acctgccaga cggaaaaccg gctttccgta ttttttcag taatcttcat gacagtggga  121
atcttgtcaa acagccttgc catcgccatt ctcatgaagg catatcagag atttagacag  181
aagtccaagg catcgtttct gcttttggcc agcggcctgg taatcactga tttctttggc  241
catctcatca atggagccat agcagtattt gtatatgctt ctgataaaga atggatccgc  301
tttgaccaat caaatgtcct ttgcagtatt tttggtatct gcatggtgtt ttctggtctg  361
tgcccacttc ttctaggcag tgtgatggcc attgagcggt gtattggagt cacaaaacca  421
atatttcatt ctacgaaaat tacatccaaa catgtgaaaa tgatgttaag tggtgtgtgc  481
ttgtttgctg ttttcatagc tttgctgccc atccttggac atcgagacta taaaattcag  541
gcgtcgagga cctggtgttt ctacaacaca gaagacatca aagactggga agatagattt  601
tatcttctac ttttttcttt tctggggctc ttagcccttg gtgtttcatt gttgtgcaat  661
gcaatcacag gaattacact tttaagagtt aaatttaaaa gtcagcagca cagacaaggc  721
agatctcatc atttggaaat ggtaatccag ctcctggcga taatgtgtgt ctcctgtatt  781
tgttggagcc catttctggt gaaagaaact catctccaga tgagactttg gacttgggac  841
tttcgagtta atgctttgga ggactattgc gaaggcttga ctgtatttTG Aaatgttaca  901
atggccaaca ttggaataaa tggaaatcat tctctggaaa cctgtgaaac aacactttt  961
gctctccgaa tggcaacatg gaatcaaatc ttagatcctt gggtatatat tcttctacga 1021
aaggctgtcc ttaagaatct ctataagctt gccagtcaat gctgtggagt gcatgtcatc 1081
agcttacata tttgggagct tagttccatt aaaaattcct taaaggttgc tgctatttct 1141
gagtcaccag ttgcagagaa atcagcaagc acctag
```

FIGURE 4

FP Receptor Variant VAR-5

```
atgtccatga acaattccaa acagctagtg tctcctgcag ctgcgcttct ttcaaacaca 61
acctgccaga cggaaaaccg gctttccgta ttttttcag taatcttcat gacagtggga 121
atcttgtcaa acagccttgc catcgccatt ctcatgaagg catatcagag atttagacag 181
aagtccaagg catcgtttct gcttttggcc agcggcctgg taatcactga tttctttggc 241
catctcatca atggagccat agcagtattt gtatatgctt ctgataaaga atggatccgc 301
tttgaccaat caaatgtcct ttgcagtatt tttggtatct gcatggtgtt ttctggtctg 361
tgcccacttc ttctaggcag tgtgatggcc attgagcggt gtattggagt cacaaaacca 421
atatttcatt ctacgaaaat tacatccaaa catgtgaaaa tgatgttaag tggtgtgtgc 481
ttgtttgctg ttttcatagc tttgctgccc atccttggac atcgagacta taaaattcag 541
gcgtcgagga cctggtgttt ctacaacaca gaagacatca aagactggga agatagattt 601
tatcttctac tttttctttt tctggggctc ttagcccttg gtgtttcatt gttgtgcaat 661
gcaatcacag gaattacact tttaagagtt aaatttaaaa gtcagcagca cagacaaggc 721
agatctcatc atttggaaat ggtaatccag ctcctggcga taatgtgtgt ctcctgtatt 781
tgttggagcc catttctgcg aTAAgacact caacgagaaa tgacagaaaa acaaggtgtg 841
gatggagagg caacatgaaa gtggatcaaa caacttatac atgggtgctg gctcagacgt 901
gacacctgag gctccagaac tggaagttta tgccgtcaag ttacaatggc caacattgga 961
ataaatggaa atcattctct ggaaacctgt gaaacaacac ttttgctct ccgaatgca 1021
acatggaatc aaatcttaga tccttgggta tatattcttc tacgaaaggc tgtccttaag 1081
aatctctata agcttgccag tcaatgctgt ggagtgcatg tcatcagctt acatatttgg 1141
gagcttagtt ccattaaaaa ttccttaaag gttgctgcta tttctgagtc accagttgca 1221
gagaaatcag caagcaccta g
```

FIGURE 5

FP Receptor Variant VAR-6

```
atgtccatga acaattccaa acagctagtg tctcctgcag ctgcgcttct ttcaaacaca 61
acctgccaga cggaaaaccg gctttccgta ttttttcag taatcttcat gacagtggga 121
atcttgtcaa acagccttgc catcgccatt ctcatgaagg catatcagag atttagacag 181
aagtccaagg catcgtttct gcttttggcc agcggcctgg taatcactga tttctttggc 241
catctcatca atggagccat agcagtattt gtatatgctt ctgataaaga atggatccgc 301
tttgaccaat caaatgtcct ttgcagtatt tttggtatct gcatggtgtt ttctggtctg 361
tgcccacttc ttctaggcag tgtgatggcc attgagcggt gtattggagt cacaaaacca 421
atatttcatt ctacgaaaat tacatccaaa catgtgaaaa tgatgttaag tggtgtgtgc 481
ttgtttgctg ttttcatagc tttgctgccc atccttggac atcgagacta taaaattcag 541
gcgtcgagga cctggtgttt ctacaacaca gaagacatca aagactggga agatagattt 601
tatcttctac tttttctttt tctggggctc ttagcccttg tgtttcatt gttgtgcaat 661
gcaatcacag gaattacact tttaagagtt aaatttaaaa gtcagcagca cagacaaggc 721
agatctcatc atttggaaat ggtaatccag ctcctggcga taatgtgtgt ctcctgtatt 781
tgttggagcc catttctgac acattggggt aaagaaattc caTGAtccct cctgtgccta 841
agccacccca gtggacctgg tcttcttgca ccatccctgt ggctggaggt ttgagatact 901
gacagcgata agacactcaa cgagaaatga cagaaaaaca aggtgtggat ggagaggcaa 961
catgaaagtg gatcaaacaa cttatacatg ggtgctggct cagacgtgac acctgaggct 1021
ccagaactgg aagtttatgc cgtcaagtta caatggccaa cattggaata aatggaaatc 1081
attctctgga aacctgtgaa acaacacttt ttgctctccg aatggcaaca tggaatcaaa 1141
tcttagatcc ttgggtatat attcttctac gaaaggctgt ccttaagaat ctctataagc 1221
ttgccagtca atgctgtgga gtgcatgtca tcagcttaca tatttgggag cttagttcca 1281
ttaaaaattc cttaaaggtt gctgctattt ctgagtcacc agttgcagag aaatcagcaa 1321
gcacctag
```

FIGURE 6

```
FP WT  MSMNNSKQLV  SPAAALLSNT  TCQTENRLSV  FFSVIFMTVG  ILSNSLAIAI  LMKAYQRFRQ  KSKASFLLLA
VAR-1  MSMNNSKQLV  SPAAALLSNT  TCQTENRLSV  FFSVIFMTVG  ILSNSLAIAI  LMKAYQRFRQ  KSKASFLLLA
VAR-2  MSMNNSKQLV  SPAAALLSNT  TCQTENRLSV  FFSVIFMTVG  ILSNSLAIAI  LMKAYQRFRQ  KSKASFLLLA
VAR-3  MSMNNSKQLV  SPAAALLSNT  TCQTENRLSV  FFSVIFMTVG  ILSNSLAIAI  LMKAYQRFRQ  KSKASFLLLA
VAR-4  MSMNNSKQLV  SPAAALLSNT  TCQTENRLSV  FFSVIFMTVG  ILSNSLAIAI  LMKAYQRFRQ  KSKASFLLLA
VAR-5  MSMNNSKQLV  SPAAALLSNT  TCQTENRLSV  FFSVIFMTVG  ILSNSLAIAI  LMKAYQRFRQ  KSKASFLLLA
VAR-6  MSMNNSKQLV  SPAAALLSNT  TCQTENRLSV  FFSVIFMTVG  ILSNSLAIAI  LMKAYQRFRQ  KSKASFLLLA

SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP
       SGLVITDFFG  HLINGAIAVF  VYASDKEWIR  FDQSNVLCSI  FGICMVFSGL  CPLLLGSVMA  IERCIGVTKP

IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
       IFHSTKITSK  HVKMMLSGVC  LFAVFIALLP  ILGHRDYKIQ  ASRTWCFYNT  EDIKDWEDRF  YLLLFSFLGL
                                                                       ↓
       LALGVSLLCN  AITGITLLRV  KFKSQQHRQG  RSHHLEMVIQ  LLAIMCVSCI  CWSPFLVTMA  NIGINGNHSL
       LALGVSLLCN  AITGITLLRV  KFKSQQHRQG  RSHHLEMVIQ  LLAIMCVSCI  CWSPFLGYRI  ILNGKEKYKV
       LALGVSLLCN  AITGITLLRV  KFKSQQHRQG  RSHHLEMVIQ  LLAIMCVSCI  CWSPFLKIEG  KIKVT-----
       LALGVSLLCN  AITGITLLRV  KFKSQQHRQG  RSHHLEMVIQ  LLAIMCVSCI  CWSPFLGYRI  ILNGKEKYKV
       LALGVSLLCN  AITGITLLRV  KFKSQQHRQG  RSHHLEMVIQ  LLAIMCVSCI  CWSPFLVKET  HLQMRLWTWD
       LALGVSLLCN  AITGITLLRV  KFKSQQHRQG  RSHHLEMVIQ  LLAIMCVSCI  CWSPFLR---  ----------
       LALGVSLLCN  AITGITLLRV  KFKSQQHRQG  RSHHLEMVIQ  LLAIMCVSCI  CWSPFLTHWG  KEIP------

ETCETTLFAL  RMATWNQILD  PWVYILLRKA  VLKNLYKLAS  QCCGVHVISL  HIWELSSIKN  SLKVAAISES
       YEEQSDFLHR  LQWPTLE---  ----------  ----------  ----------  ----------  ----------
       ----------  ----------  ----------  ----------  ----------  ----------  ----------
       YEEQSDFLHR  K---------  ----------  ----------  ----------  ----------  ----------
       FRVNALEDYC  EGLTVF----  ----------  ----------  ----------  ----------  ----------
       ----------  ----------  ----------  ----------  ----------  ----------  ----------
       ----------  ----------  ----------  ----------  ----------  ----------  ----------

PVAEKSAST
       ---------
       ---------
       ---------
       ---------
       ---------
       ---------
```

HUMAN PROSTAGLANDIN FP RECEPTOR VARIANTS AND METHODS OF USING SAME

BACKGROUND OF THE INVENTION

This invention relates generally to molecular medicine and, more specifically, to alternatively spliced prostaglandin FP receptors.

Prostaglandins (PG) and thromboxane, collectively named prostanoids, are oxygenated fatty acids that bind to seven transmembrane domain G-protein coupled receptors (GPCRs). The classification of prostanoid receptors into DP, EP, FP, IP, and TP is based on the binding and functional potency of the five naturally occurring prostanoids, $PGD_2$, $PGE_2$, $PGF_{2\alpha}$, $I_2$, and $TXA_2$, respectively. Prostanoid receptors have been cloned and expressed in cultured cells, where ligand binding and signal transduction properties have been studied. It is recognized that prostanoids can bind to more than one prostanoid receptor type; however, each prostanoid binds to its respective receptor with an affinity at least one order of magnitude higher than its affinity for the other four prostanoid receptors.

Prostanoids produce numerous physiologic and pathophysiologic effects and regulate cellular processes in nearly every tissue. The wide spectrum of prostanoid action includes effects on immune, endocrine, cardiovascular, renal and reproductive systems as well as the contraction and relaxation of smooth muscle. Accordingly, prostanoids and prostanoid analogues have been used as drugs to treat a variety of clinical conditions, including, but not limited to, conditions associated with the female reproductive system.

One of the clinically important prostanoid receptors is the FP receptor. This receptor is expressed in a range of different species and in a variety of different tissues, including, without limitation, eye, small intestine, corpus luteum, placenta, ovary, brain, myometrium, lung, kidney, stomach, muscle, uterus and trachea, and is particularly prevalent in the corpus luteum, where it mediates luteolysis. Consequently, $PGF_{2\alpha}$ analogues are effective agents for synchronizing the oestrus cycles of a variety of farm animals and have been used to facilitate animal husbandry.

A tissue that has proved useful in the study of the FP receptor is the iris sphincter muscle from both cat and dog. The presence of the FP receptor in ocular tissue has important pharmacological consequences, and $PGF_{2\alpha}$ analogues such as latanoprost have proven effective in lowering intraocular pressure in various species, including humans, where they are used to treat conditions such as glaucoma.

While $PGF_{2\alpha}$ is a potent FP receptor agonist, it is rather non-selective, having appreciable agonist activity at EP and TP receptors. Although analogues of $PGF_{2\alpha}$ have been synthesized that have reduced agonist activity at other prostanoid receptors, the $PGF_{2\alpha}$ agonist drugs currently available still have some agonist activity at other receptors, which can result in undesirable side effects. For example, an ocular side effect of the $PGF_{2\alpha}$ analogue latanoprost is increased iris pigmentation, which is due to increased synthesis of melanin in the melanocytes of the iris stroma. In addition, a low frequency of cystoid macular edema has been reported with this drug, usually in predisposed eyes. Such side effects may be due in part to a lack of receptor specificity.

A goal of clinical pharmacology and the pharmaceutical industry is the development of more selective drugs with greater efficacy and fewer side effects than those currently in use. In order to more effectively treat conditions where FP receptor modulators can be of benefit such as glaucoma, new receptors related to the known wild-type FP receptor must be discovered and used to design screening assays for identification of compounds that bind more specifically to the known FP receptor. Newly identified FP receptors such as alternatively spliced FP receptors can be more closely associated with a disease such as glaucoma than the known FP receptor and can be targets for drug discovery efforts, resulting in the development of drugs having greater efficacy or fewer side effects than drugs developed against the known wild-type FP receptor.

Thus, there exists a need for the discovery of new FP receptors which can be used, for example, to design more specific drugs with fewer side effects. The present invention satisfies this need and provides related advantages as well.

SUMMARY OF THE INVENTION

The invention provides an isolated polypeptide containing the amino acid sequence of SEQ ID NO: 17, 18, 19, 20, 21, 22, 23, 24, or 25. The invention also provides an isolated polypeptide containing an amino acid sequence having at least 50% amino acid identity with SEQ ID NO: 14 and an amino acid sequence of SEQ ID NO: 17, 18, 19, 20, 21, 22, 23, 24, or 25, or a conservative variant thereof. The invention further provides an isolated polypeptide containing the amino acid sequence of SEQ ID NO: 2, 4, 6, 8, 10, or 12. The invention also provides a method for identifying a compound that modulates a FP receptor variant by contacting an isolated FP receptor variant or a FP receptor variant overexpressed in a genetically engineered cell with a compound and determining the level of an indicator which correlates with modulation of a FP receptor variant, where an alteration in the level of the indicator as compared to a control level indicates that the compound is a compound that modulates the FP receptor variant.

BRIEF DESCRIPTION OF THE DRAWINGS

FIG. 1 shows the nucleotide sequence of FP receptor variant VAR-1 (SEQ ID NO: 1). The underlined sequence indicates novel nucleotide sequence compared to the nucleotide sequence of the known wild-type human FP receptor (SEQ ID NO: 13). The stop codon for FP receptor variant VAR-1 is indicated in capital letters.

FIG. 2 shows the nucleotide sequence of FP receptor variant VAR-2 (SEQ ID NO: 3). The underlined sequence indicates novel nucleotide sequence compared to the nucleotide sequence of the known wild-type human FP receptor (SEQ ID NO: 13). The stop codon for FP receptor variant VAR-2 is indicated in capital letters.

FIG. 3 shows the nucleotide sequence of FP receptor variant VAR-3 (SEQ ID NO: 5). The underlined sequence indicates novel nucleotide sequence compared to the nucleotide sequence of the known wild-type human FP receptor (SEQ ID NO: 13). The stop codon for FP receptor VAR-3 is indicated in capital letters.

FIG. 4 shows the nucleotide sequence of FP receptor variant VAR-4 (SEQ ID NO: 7). The underlined sequence indicates novel nucleotide sequence compared to the nucleotide sequence of the known wild-type human FP receptor (SEQ ID NO: 13). The stop codon for FP receptor variant VAR-4 is indicated in capital letters.

FIG. 5 shows the nucleotide sequence of FP receptor variant VAR-5 (SEQ ID NO: 9). The underlined sequence indicates novel nucleotide sequence compared to the nucleotide sequence of the known wild-type human FP receptor (SEQ ID NO: 13). The stop codon for FP receptor variant VAR-5 is indicated in capital letters.

FIG. 6 shows the nucleotide sequence of FP receptor variant VAR-6 (SEQ ID NO: 11). The underlined sequence indicates novel nucleotide sequence compared to the nucleotide sequence of the known wild-type human FP receptor (SEQ ID NO: 13). The stop codon for FP receptor variant VAR-6 is indicated in capital letters.

FIG. 7 shows a comparison of the amino acid sequences of the known wild-type human FP receptor (SEQ ID NO: 14), abbreviated as FP WT, with human FP receptor variants VAR-1 (SEQ ID NO: 2), VAR-2 (SEQ ID NO: 4), VAR-3 (SEQ ID NO: 6), VAR-4 (SEQ ID NO: 8), VAR-5 (SEQ ID NO: 10), and VAR-6 (SEQ ID NO: 12). An arrow in the carboxy terminal area of the polypeptides indicates the location where the wild-type human FP receptor and the FP receptor variants VAR-1 through VAR-6 begin to differ.

DETAILED DESCRIPTION OF THE INVENTION

The present invention is directed to the exciting discovery of several novel FP receptor variants. Such FP receptor variants can be used to determine and refine the specificity of binding of compounds that bind to the known wild-type FP receptor. These FP receptor variants also can be used to identify compounds that differentially modulate or bind to a first FP receptor variant in relation to a second FP receptor variant or wild-type FP receptor. Such a compound can be, for example, a ligand that specifically binds to a novel FP receptor variant described herein.

As disclosed herein in Example I, several novel FP receptor variants were identified using the reverse transcription polymerase chain reaction (RT-PCR) and the following FP receptor primers: TGCAATGCAATCACAGGAAT (SEQ ID NO: 15) and CACTCCACAGCATTGACTGG (SEQ ID NO: 16). In particular, six novel alternatively spliced FP receptor variants, referred to herein as human FP receptor variants VAR-1 through VAR-6, were identified as distinct from the wild-type human FP receptor (see FIGS. 1-6).

Figure 8:
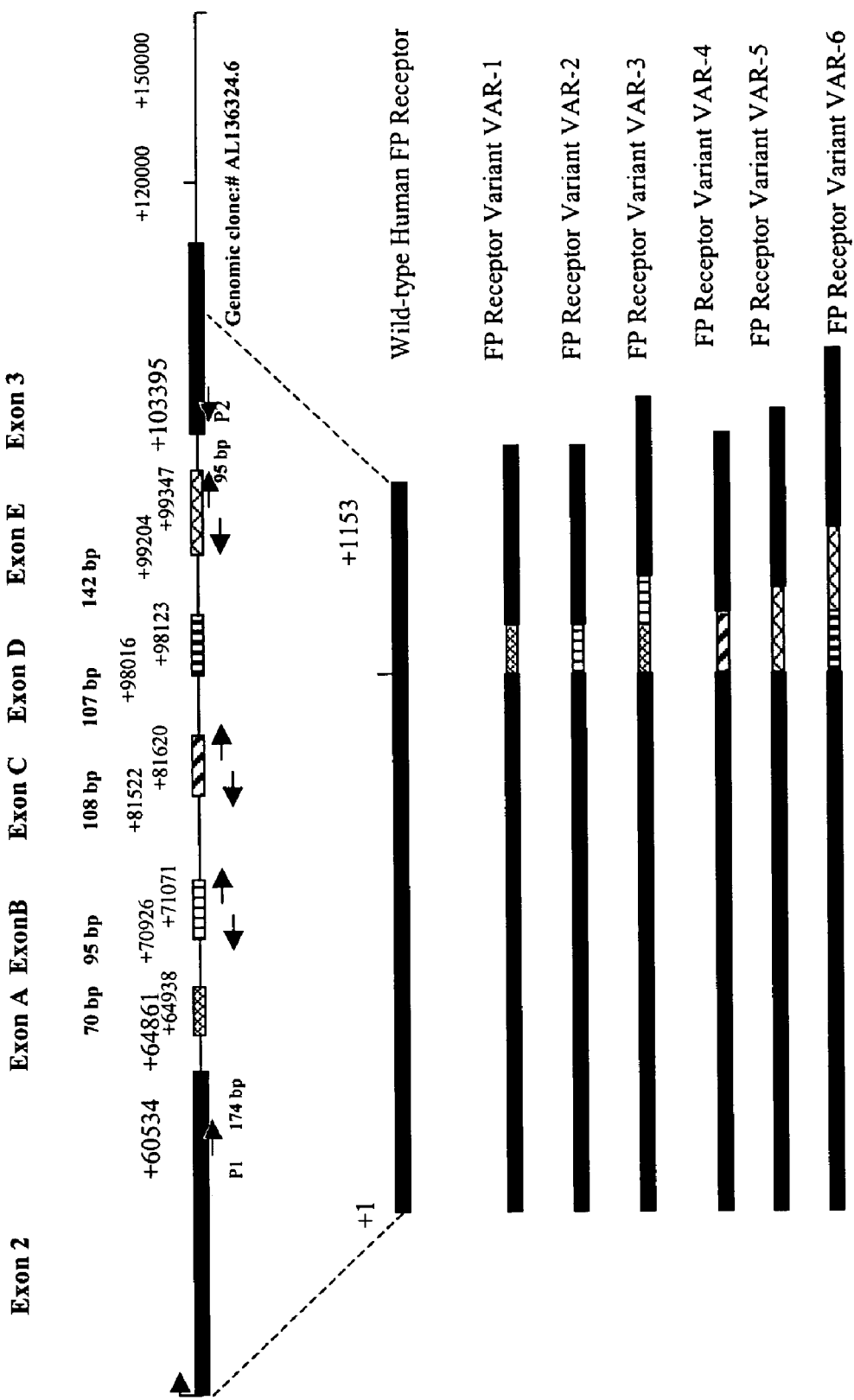
FIG. 8 shows the intron/exon structure of human FP receptor genomic DNA clone AL 136324.6. The location of exons 2 and 3, which are conserved between the wild-type human FP receptor and the FP receptor variants VAR-1 through VAR-6, are shown as well as the size and nucleotide end points of alternatively spliced exons A, B, C, D and E. The figure schematically indicates which exons are found in FP receptor variants VAR-1 through VAR-6.

As further disclosed herein, sequence analysis of nucleic acid molecules encoding the alternatively spliced FP receptor variants revealed novel carboxy-terminal amino acid sequence. The amino acid sequences of the wild-type human FP receptor and the alternatively spliced FP receptor variants are shown in FIG. 7. As shown in FIG. 8, exons 2 and 3 are conserved between the known wild-type FP receptor and the alternatively spliced FP receptors while the alternatively spliced FP receptors additionally contain one or more alternatively spliced exons (exons A, B, C, D, or E). Comparison of the known wild-type human FP receptor amino acid sequence (SEQ ID NO: 14) to the alternatively spliced human FP receptor variants revealed the amino acid sequence at the junction between conserved exon 2 and the relevant alternatively spliced exon (exon A) within FP receptor variant VAR-1 and FP receptor variant VAR-3 to be SPFLGYRII (SEQ ID NO: 17), where the first four amino acids correspond to amino acid sequence present in conserved exon 2 and the remaining five amino acids are residues derived from newly identified exon A which is present in FP receptor variants VAR-1 and VAR-3 (see FIGS. 7 and 8). Similarly, the amino acid sequence at the junction between conserved exon 2 and the relevant alternatively spliced exon (exon B) within FP receptor variant VAR-2 is SPFLKIEGK (SEQ ID NO: 18); the amino acid sequence at the junction between conserved exon 2 and the relevant alternatively spliced exon (exon C) within FP receptor variant VAR-4 is SPFLVKETH (SEQ ID NO: 19); and the amino acid sequence at the junction between conserved exon 2 and the relevant alternatively spliced exon (exon D) within FP receptor variant VAR-6 is SPFLTHWGK (SEQ ID NO: 20), where the first four amino acids correspond to amino acid sequence present in conserved exon 2 and the remaining five amino acids are residues derived from the newly identified exons present in the particular alternatively spliced FP receptor variant.

Figure 9A:
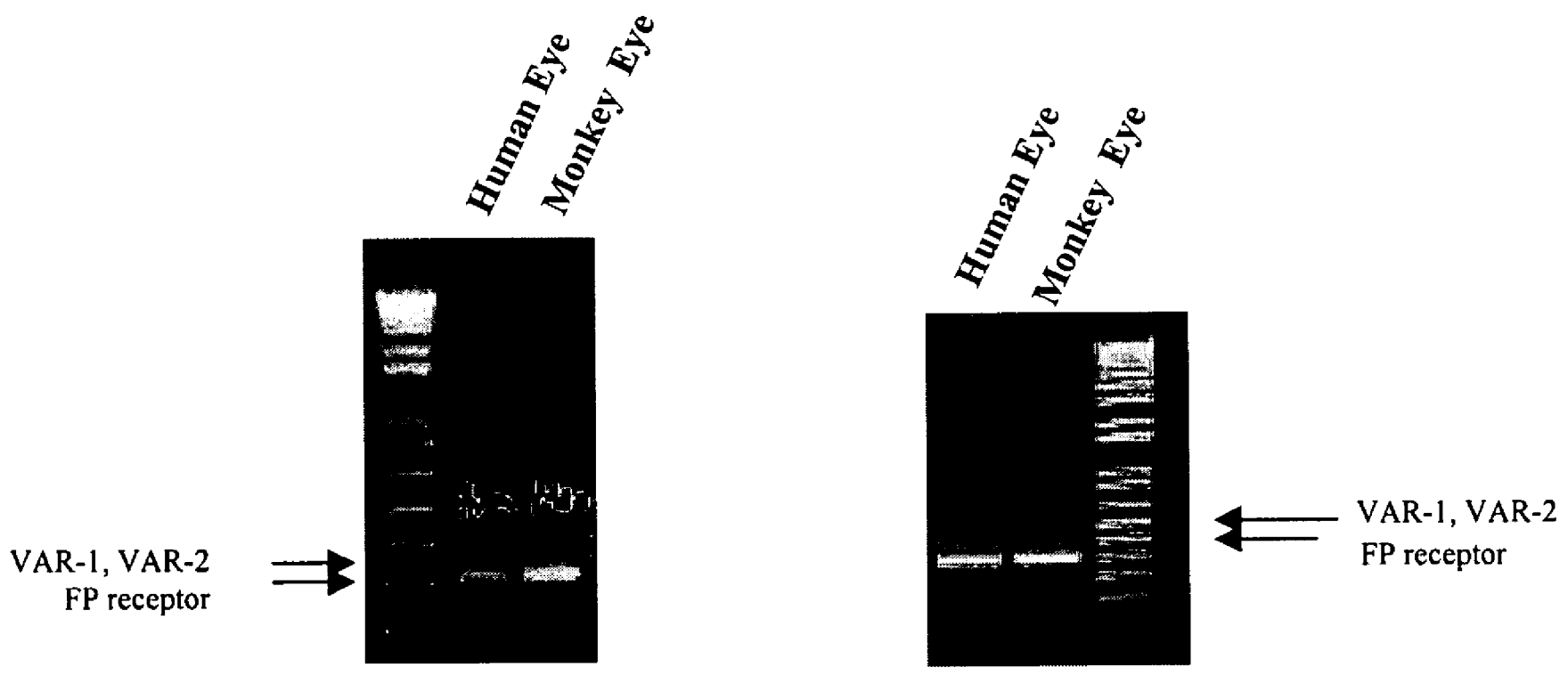
Figure 9B:
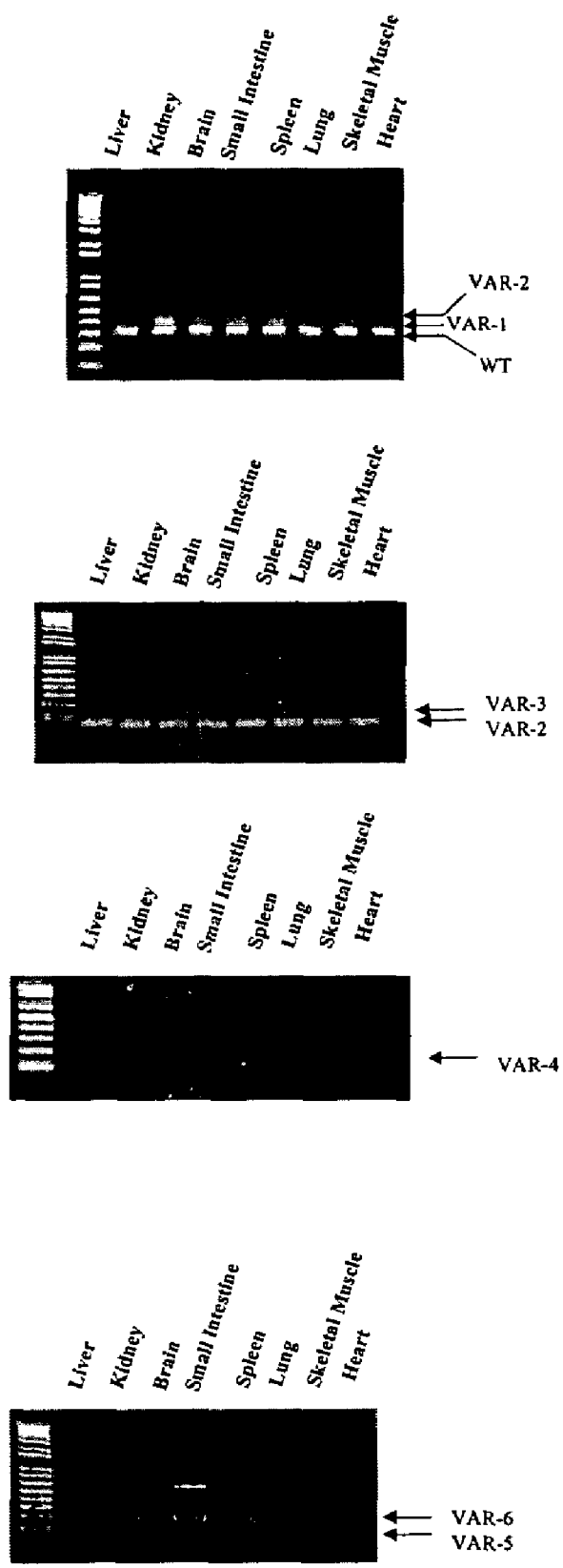
FIGS. 9 A and B show distribution of mRNA from FP receptor variants VAR-1 through VAR-6 in various tissues using an RT-PCR procedure. The location of PCR products of the correct size for FP receptor variants VAR-1 through VAR-6 is indicated by an arrow. WT indicates the wild-type human FP receptor. A. Detection of mRNA from FP receptor variants and the known wild-type FP receptor in human and monkey eye tissue. B. Detection of mRNA from FP receptor variants VAR-1 through VAR-6 in various human tissues.

As further disclosed herein in FIG. 7, the carboxy terminal amino acid sequence in FP receptor variants VAR-1 through VAR-6 is unique to the respective FP receptor variant. Specifically, the unique carboxy terminus of FP receptor variant VAR-1 has the amino acid sequence GYRIILNGKEKYKVYEEQSDFLHRLQWPTLE (SEQ ID NO: 21); the unique carboxy terminus of FP receptor variant VAR-2 has the amino acid sequence KIEGKIKVT (SEQ ID NO: 22); the unique carboxy terminus of FP receptor variant VAR-3 has the amino acid sequence GYRIILNGKEKYKVYEEQSDFLHRK (SEQ ID NO: 23); the unique carboxy terminus of FP receptor variant VAR-4 has the amino acid sequence VKETHLQMRLWTWDFRVNALEDYCEGLTVF (SEQ ID NO: 24); the unique carboxy terminus of FP receptor variant VAR-5 contains just one amino acid, an arginine; and the unique carboxy terminus of FP receptor variant VAR-6 has the amino acid sequence THWGKEIP (SEQ ID NO: 25). Furthermore, expression of alternatively spliced human FP receptor variants VAR-1 through VAR-6 can be found in a variety of tissues including human eye, liver, kidney, brain, small intestine, spleen, lung, skeletal muscle, heart, and monkey eye (see FIG. 9 and Example II).

Based on these discoveries, the present invention provides novel alternatively spliced FP receptor variants and screening methods that rely on these variants. In particular, the invention provides an isolated polypeptide containing one of the following amino acid sequences: SEQ ID NO: 17, 18, 19, 20, 21, 22, 23, 24, or 25, which represent the unique junctional and carboxy-terminal portions of newly identified FP variants VAR-1 to VAR-6. The present invention further provides an isolated polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. Also provided herein is an isolated polypeptide containing the amino acid sequence of SEQ ID NO: 2, 4, 6, 8, 10, or 12.

The present invention further provides a method for identifying a compound that modulates a FP receptor variant by contacting an isolated FP receptor variant or a FP receptor variant over-expressed in a genetically engineered cell with a compound and determining the level of an indicator which correlates with modulation of a FP receptor variant, where an alteration in the level of the indicator as compared to a control level indicates that the compound is a compound that modulates the FP receptor variant. The present invention also provides a method for identifying a compound that specifically binds to a FP receptor variant by contacting an isolated FP receptor variant or a FP receptor variant over-expressed in a genetically engineered cell with a compound and determining specific binding of the compound to the FP receptor variant.

The invention further provides a method for identifying a compound that differentially modulates a FP receptor variant by a) contacting an isolated FP receptor variant or a FP receptor variant over-expressed in a genetically engineered cell with a compound; b) determining the level of an indicator which correlates with modulation of a FP receptor variant; c) contacting a second receptor with the compound; d) determining the level of a corresponding indicator after contacting of the compound to the second receptor; and e) comparing the level of the indicator from step (b) with the level of the corresponding indicator from step (d), where a different level of the indicator from step (b) compared to the level of the corresponding indicator from step (d) indicates that the compound is a compound that differentially modulates the FP receptor variant.

Further provided herein is a method for identifying a compound that differentially binds to a FP receptor variant by a) contacting an isolated FP receptor variant or a FP receptor variant over-expressed in a genetically engineered cell with a compound; b) determining specific binding of the compound to the FP receptor variant; c) contacting a second receptor with the compound; d) determining specific binding of the compound to the second receptor; and e) comparing the level of specific binding from step (b) with the level of specific binding from step (d), where a different level of specific binding from step (b) compared to the level of specific binding from step (d) indicates that the compound is a compound that differentially binds to the FP receptor variant.

The methods of the invention can be useful for designing drugs that bind to or modulate the wild-type human FP receptor (SEQ ID NO: 14) in preference to one or more alternatively spliced variants or for identifying compounds that bind to or modulate one or more FP receptor variants in preference to other FP receptor variants or the wild type FP receptor. Compounds identified by a method of the invention can be therapeutically useful in preventing or reducing the severity of a condition where modulation of a FP receptor or a FP receptor variant is beneficial.

The present invention relates to novel FP receptor variants related to the wild-type FP receptor, which has been cloned from several species including mouse (Sugimoto et al., *J. Biol. Chem.* 269:1356-1360 (1994)), rat (Kitanaka et al., *Prostaglandins* 48:31-41 (1994); Lake et al., *FEBS Lett.* 355:317-325 (1994)), sheep (Graves et al., *Endocrinology* 136:3430-3436 (1995)), cow (Sakamoto et al., *J. Biol. Chem.* 269:3881-3886 (1994)), and human (Lake et al., supra, 1994; Abramovitz et al., *J. Biol. Chem.* 269:2632-2636 (1994)). The sequence of wild-type FP receptors from various species such as human (GenBank Accession No. NM_000959), mouse (GenBank Accession No. P43117), rat (GenBank Accession No. NP_037247), cat (GenBank Accession No. AAL36977), sheep (GenBank Accession No. Q28905), cow (GenBank Accession No. BAA20871) and monkey (GenBank Accession No. AAB36298) are known in the art.

FP receptor gene structure has been evaluated in several mammalian species including human (Duncan et al., *Genomics* 25:740-742 (1995); Betz et al., *Biochem. Biophys. Res. Commun.* 254:413-416 (1999)), murine (Ishikawa et al., *Genomics* 32:285-288 (1996); Hasumoto et al., *Genes Cells* 2:571-580 (1997)), and bovine (Ezashi et al., *Gene* 190:271-278 (1996)). A single gene encodes the FP receptor, with a size of approximately 10 kilobases (kb) in human, 11 kb in mouse, and 40 kb in cow. In humans, the genes for the FP receptor and PGE receptor-subtype 3 have been localized to the short arm of chromosome 1 (Duncan et al., supra, 1995). The mouse FP receptor gene has been mapped to the distal end of chromosome 3 near the gene for the PGE receptor-subtype 3 (Ishikawa et al., supra, 1996; Taketo et al., *Genomics* 19:585-588 (1994)).

The exon/intron organization of the FP receptor gene is conserved among humans, mice, and cattle and is similar to other prostanoid receptor genes (Ogawa et al., *Genomics* 27:142-148 (1995)). The FP receptor gene has been reported to consist of three exons and two introns, with the translated region located in exons 2 and 3 (Betz et al., supra, 1999; Hasumoto et al., supra, 1997; Ezashi et al., supra, 1996). The first exon is relatively short (160 to 194 bp) and includes most of the 5' untranslated region. Intron 1 ranges in size from 1.3 to 1.5 kb and can include important promoter sequences. The second exon (868 to 870 bp) contains an untranslated region of approximately 70 bp and the majority of the translated receptor. The large second intron (6.1 to 33 kb) interrupts the translated region at the sixth transmembrane domain (Betz et al., supra, 1999; Hasumoto et al., supra, 1997; Ezashi et al., supra, 1996). The splice junction located in the sixth transmembrane domain is also conserved among other PG receptor genes, such as the human PGE receptor-subtype 3, prostacyclin receptor and thromboxane receptor (Ogawa et al., supra, 1995). The third exon (1066 to 3977 bp) includes the remainder of the translated region of the wild-type FP receptor and a large 3' untranslated region (Betz et al., supra, 1999; Hasumoto et al., supra, 1997; Ezashi et al., supra, 1996). Alternatively spliced forms of the FP receptor have been found in cow (GenBank Accession Nos. AB083784, AB083785, AB083786, AB083787 and AB083788) and sheep (Pierce et al., *J. Biol. Chem.* 272:883-887 (1997)). Novel alternatively spliced forms of the human FP receptor are disclosed herein.

Expression of mRNA encoding the FP receptor has been evaluated in a variety of tissues using Northern blot hybridization (Sugimoto et al., supra, 1994; Kitanaka et al., supra, 1994; Lake et al., supra, 1994; Graves et al., supra, 1995; Sakamoto et al., supra, 1994; Juengel et al., *Biol. Reprod.* 54:1096-1102 (1996); Sakamoto et al., *J. Reprod. Fertil.* 103:99-105 (1995); Rueda et al., *Endocrine* 3:781-787 (1995)) and quantitative, competitive reverse transcriptase-polymerase chain reaction (Tsai et al., *Endocrinology* 137:3348-3355 (1996); Tsai et al., *J. Reprod. Fertil.* 114:69-75 (1998); Tsai and Wiltbank, *Biol. Reprod.* 58:346-352 (1998)). As discussed above, the FP receptor is expressed in a variety of tissues including eye, small intestine, corpus luteum, placenta, ovary, brain, myometrium, lung, kidney, stomach, muscle, uterus and trachea.

The size of the FP receptor protein is similar among different species, with estimated molecular weights ranging from 40,060 Da (human) to 40,983 Da (bovine) (Sakamoto et al., supra, 1995; Abramovitz et al., supra, 1994). The wild-type bovine and ovine FP receptors contain 362 amino acid residues in the open reading frame (Graves et al., supra, 1995; Sakamoto et al., supra, 1994), while mouse and rat FP receptors have 366 amino acids (Sugimoto et al., supra, 1994; Kitanaka et al., supra, 1994), and the human FP receptor contains 359 amino acids (Abramovitz et al., supra, 1994). The bovine FP receptor (Sakamoto et al., supra, 1995) shares 98% homology with the ovine FP receptor (Graves et al., supra, 1995), 86% with the human FP receptor (Abramovitz et al., supra, 1994), 80% with the mouse FP receptor (Sugimoto et al., supra, 1994), and 78% with the rat FP receptor (Kitanaki et al., supra, 1994). In these five species, 272 out of 362 amino acids (75.1%) in the FP receptor are identical.

The FP receptor is a member of the seven transmembrane G-protein-coupled receptor (GPCR) family of receptors. The three-dimensional structure of the GPCR ligand bacteriorhodopsin revealed by electron cryomicroscopy and mutational data on the $\beta_2$-adrenergic receptor (Henderson et al., *J. Mol. Biol.* 213:899-929 (1990)) have allowed construction of three-dimensional models for several mammalian GPCRs, including human thromboxane $A_2$ ($TXA_2$) receptor (TP) (Yamamoto et al., *J. Med. Chem.* 36:820-825 (1993)) and subsequently the bovine FP receptor (Sakamoto et al., *J. Lipid Mediat. Cell Signal* 12:405-411 (1995)). Based on the fact that $\alpha$-helices contain 3.6 residues per helical turn, sequence analysis shows that the transmembrane domains of GPCRs contain a predominance of hydrophobic residues on one side of each $\alpha$-helix and hydrophilic residues on the other side (Engelman and Zaccai, *Proc. Natl. Acad. Sci. USA* 77:5894-5898 (1980); Probst et al., *DNA Cell Biol.* 11:1-20 (1992)). It has been postulated that the hydrophilic residues of the seven helices face each other, thus forming a ligand binding pocket, while the hydrophobic residues face the lipid bilayer (Yamamoto et al., supra, 1993; Engelman and Zaccai, supra, 1980; Probst et al., supra, 1992). Some amino acids located on the hydrophilic sides of the seventh transmembrane domain of GPCRs can be important in ligand binding and are highly conserved in all prostaglandin receptors.

As observed in other GPCRs (Probst et al., supra, 1992), two potential N-glycosylation sites (Asn-4 and Asn-19) are found in the amino-terminal region of the FP receptor (Sugimoto et al., supra, 1994; Kitanaka et al., supra, 1994; Lake et al., supra, 1994; Graves et al, supra, 1995; Sakamoto et al., supra, 1994; Abramovitz et al., supra, 1994). Six serine or threonine residues in the FP receptor have been suggested as potential phosphorylation sites for protein kinase C. Of these two are in the second intracellular loop while four are found in the carboxy-terminal end of the receptor. Cysteine residues in the first and second extracellular loops of the FP receptor can form a disulfide bond that can stabilize the protein structure (Lake et al., supra, 1994; Abramovitz et al., supra, 1994; Probst et al., supra, 1992). These two cysteines are highly conserved among all prostaglandin receptors. Three prolines in transmembrane domains IV, VI, and VII can introduce kinks in the $\alpha$-helices which can contribute to the ligand binding pocket (Yamamoto et al., supra, 1993; Probst et al., supra, 1992; Applebury and Hargrave, *Vision Res.* 26.1881-1895 (1986); Findlay and Eliopoulos, *Trends Pharmacol. Sci.* 11:492-499 (1990)).

Cross-reactivity can occur between various protaglandins and specific prostaglandin receptors, although the extent of such cross-reactivity varies among different species and studies (Anderson et al., *J. Reorod. Fertil.* 115:133-141 (1999); Griffin et al., *J. Pharmacol. Exo. Ther.* 281:845-854 (1997); Kiriyama et al., *Br. J. Pharmacol.* 122:217-224 (1997)).

Cross-reactivity of prostaglandins and prostaglandin receptors is due in part to similarity in structure of the prostaglandin molecules. Certain key sites, such as the C1 carboxylic acid and the C15 hydroxyl, are conserved among many prostaglandins and appear to be important for binding to any prostaglandin receptor. The C15 position plays a role in prostaglandin metabolism; enzymatic dehydrogenation of C15 by 15-hydroxy-prostaglandin dehydrogenase present in lung, liver, kidney and corpus luteum results in prostaglandin inactivation (Änggård and Samuelsson, *J. Biol. Chem.* 239:4097-4102 (1964); Silva et al., *Biol. Reprod.* 63:1229-1236 (2000)). Furthermore, changing the hydroxyl at the 15th carbon to 15-keto $PGF_{2\alpha}$ or 15-methyl $PGF_{2\alpha}$ decreases binding affinity to the FP receptor (Anderson et al., supra, 1999). Sites that differ between prostaglandins, such as C9 and C11, can be important for specificity of receptor binding.

Binding of a prostaglandin agonist such as $PGF_{2\alpha}$ to a FP receptor can activate numerous intracellular effector systems including, without limitation, the trimeric G-proteins $G\alpha_q$ and $G\alpha_{11}$ (Carrasco et al., *J. Repr. Fertil.* 111:309-317 (1997)), the small G-protein Rho (Pierce et al., *J. Biol. Chem.* 274:35944-35949 (1999)), phospholipase C (Gusovsky, *Mol. Pharmacol.* 40:633-638 (1991); Boiti et al., *J. Endocrinol.* 164:179-186 (2000)), inositol triphosphate/free intracellular calcium (Davis et al., *Proc. Natl. Acad. Sci. USA* 84:3728-3732 (1987); Wiltbank et al., *Biol. Reprod.* 41:771-778 (1989)), phospholipase D (Liu et al., *Prostaglandins* 51:233-248 (1996)), and mitogen-activated protein kinases (Chen et al., *Endocrinology* 139:3876-3885 (1998); Niswender et al., *Physiol. Rev.* 80:1-29 (2000)).

The invention provides novel FP receptor variants which are alternatively spliced forms of the wild-type FP receptor. In one embodiment, the invention provides an isolated polypeptide having one of the following amino acid sequences: SEQ ID NO: 17, 18, 19, 20, 21, 22, 23, 24, or 25. In another embodiment, the invention provides an isolated polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. In a further embodiment, the invention provides an isolated polypeptide containing the amino acid sequence of SEQ ID NO: 2, 4, 6, 8, 10, or 12. In still a further embodiment, the invention provides an isolated polypeptide that consists of the amino acid sequence of SEQ ID NO: 2, 4, 6, 8, 10, or 12.

The invention further provides a FP receptor variant binding agent which binds the amino acid sequence of SEQ ID NO: 21, 22, 23, 24, or 25, or an epitope thereof. Such a FP receptor variant binding agent can be, without limitation, an antibody or antigen binding fragment thereof. The invention additionally provides a cell that includes an exogenously expressed polypeptide containing the amino acid sequence of SEQ ID NO: 17, 18, 19, 20, 21, 22, 23, 24, or 25; a cell which includes an exogenously expressed polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; and a cell which includes an exogenously expressed polypeptide containing the amino acid sequence of SEQ ID NO: 2, 4, 6, 8, 10, or 12.

The present invention also provides a method for identifying a compound that modulates a FP receptor variant by contacting an isolated FP receptor variant or a FP receptor variant over-expressed in a genetically engineered cell with a compound and determining the level of an indicator which correlates with modulation of a FP receptor variant, where an alteration in the level of the indicator as compared to a control level indicates that the compound is a compound that modulates the FP receptor variant. The alteration can be, for example, an increase or decrease in the level of an indicator such as, without limitation, calcium. A method of the invention can be practiced with any of a variety of FP receptor variants such as an isolated polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or an isolated polypeptide containing the amino acid sequence of SEQ ID NO: 2, 4, 6, 8, 10, or 12. A method of the invention also can be practiced using any of a variety of FP receptor variants over-expressed in a genetically engineered cell. In one embodiment, the FP receptor variant is exogenously over-expressed in the genetically engineered cell. A variety of compounds can be screened according to the methods of the invention including, but not limited to, polypeptides and small molecules.

The present invention further provides a method for identifying a compound that specifically binds to a FP receptor variant by contacting an isolated FP receptor variant or a FP receptor variant over-expressed in a genetically engineered cell with a compound and determining specific binding of the compound to the FP receptor variant. In particular embodiments, a method of the invention is practiced using an isolated FP receptor variant such as a polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or an isolated FP receptor variant containing the amino acid sequence of SEQ ID NO: 2, 4, 6, 8, 10, or 12. In another embodiment, a method of the invention is practiced using a FP receptor variant over-expressed in a genetically engineered cell, for example, a FP receptor variant exogenously over-expressed in a genetically engineered cell. In the methods of the invention, contacting can occur in vivo or in vitro, and the compounds to be screened can include, without limitation, polypeptides and small molecules.

The invention further provides a method for identifying a compound that differentially modulates a FP receptor variant by a) contacting an isolated FP receptor variant or a FP receptor variant over-expressed in a genetically engineered cell with a compound; b) determining the level of an indicator which correlates with modulation of a FP receptor variant; c) contacting a second receptor with the compound; d) determining the level of a corresponding indicator after contacting of the compound to the second receptor; and e) comparing the level of the indicator from step (b) with the level of the corresponding indicator from step (d), where a different level of the indicator from step (b) compared to the level of the corresponding indicator from step (d) indicates that the compound is a compound that differentially modulates the FP receptor variant. The second receptor can be, for example, a distinct FP receptor variant or a wild-type FP receptor from the same or a different species, or a functional fragment thereof. The level of the indicator from step (b) can be greater or less than the level of the indicator from step (d) and the indicator can be, for example, calcium. In particular embodiments, a method of the invention is practiced using an isolated FP receptor variant containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or with an isolated FP receptor variant containing the amino acid sequence of SEQ ID NO: 2, 4, 6, 8, 10, or 12. In another embodiment, a method of the invention is practiced using a FP receptor variant over-expressed in a genetically engineered cell, for example, a FP receptor variant exogenously over-expressed in a genetically engineered cell. In the methods of the invention, the compounds to be screened can include, without limitation, polypeptides and small molecules.

The invention further provides a method for identifying a compound that differentially binds to a FP receptor variant by a) contacting an isolated FP receptor variant or a FP receptor variant over-expressed in a genetically engineered cell with a compound; b) determining specific binding of the compound to the FP receptor variant; c) contacting a second receptor with the compound; d) determining specific binding of the compound to the second receptor; and e) comparing the level of specific binding from step (b) with the level of specific binding from step (d), where a different level of specific binding from step (b) compared to the level of specific binding from step (d) indicates that the compound is a compound that differentially binds to the FP receptor variant. The second receptor can be, for example, a distinct FP receptor variant or a wild-type FP receptor from the same or a different species, or a functional fragment thereof. The different level of specific binding can be an increased or decreased level of specific binding. In particular embodiments, a method of the invention is practiced using an isolated FP receptor variant containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or with an isolated FP receptor variant containing the amino acid sequence of SEQ ID NO: 2, 4, 6, 8, 10, or 12. In another embodiment, a method of the invention is practiced using a FP receptor variant over-expressed in a genetically engineered cell, for example, a FP receptor variant exogenously over-expressed in a genetically engineered cell. In the methods of the invention, contacting can occur in vivo or in vitro, and the compounds to be screened can include, without limitation, polypeptides and small molecules.

The invention also provides an isolated nucleic acid molecule having a nucleotide sequence that encodes a polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. The invention further provides an isolated nucleic acid molecule containing a nucleotide sequence that encodes the amino acid sequence of SEQ ID NO: 2, 4, 6, 8, 10, or 12, such as the nucleotide sequence of SEQ ID NO: 1, 3, 5, 7, 9, or 11, respectively. The invention further provides a vector containing a nucleic acid molecule having a nucleotide sequence that encodes a polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or a nucleic acid molecule containing a nucleotide sequence that encodes the amino acid sequence of SEQ ID NO: 2, 4, 6, 8, 10, or 12. Host cells containing such a vector are further provided herein.

The invention relates, in part, to the identification of novel FP receptor variants. As used herein, the term "FP receptor variant" means a polypeptide containing an amino acid sequence that has at least 30% amino acid identity with the wild-type human FP receptor SEQ ID NO: 14 and further containing the amino acid sequence of SEQ ID NO: 17, 18, 19, 20, 21, 22, 23, 24, or 25, or a conservative variant of this amino acid sequence. A FP receptor variant can contain an amino acid sequence having, for example, at least 30% amino acid identity, at least 40% amino acid identity, at least 50% amino acid identity, at least 60% amino acid identity, at least 70% amino acid identity, at least 80% amino acid identity, at least 90% amino acid identity, or at least 95% amino acid identity with the wild-type human FP receptor SEQ ID NO: 14. As a non-limiting example, a FP receptor variant can contain an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof.

Based on the above, it is understood that species homologs of FP receptor variants that contain the amino acid sequence of SEQ ID NO: 17, 18, 19, 20, 21, 22, 23, 24, or 25, or a conservative variant thereof, are encompassed by the definition of FP receptor variant as used herein. As non-limiting examples, an isolated polypeptide containing the amino acid sequence of SEQ ID NO: 2, 4, 6, 8, 10, or 12, or consisting of the amino acid sequence of SEQ ID NO: 2, 4, 6, 8, 10, or 12 is a FP receptor variant of the invention.

A FP receptor variant differs from the known wild-type human FP receptor polypeptide by containing the amino acid sequence of SEQ ID NO: 17, 18, 19, 20, 21, 22, 23, 24, or 25, or a conservative variant of such an amino acid sequence. As used herein in reference to a specified amino acid sequence such as one of SEQ ID NOS: 17-25, a "conservative variant" is a sequence in which a first amino acid is replaced by another amino acid or amino acid analog having at least one biochemical property similar to that of the first amino acid; similar properties include, yet are not limited to, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. It is understood that a conservative variant of one of SEQ ID NOS: 17-25 can have one, two, three, four, five, six or more amino acid substitutions relative to the specified sequence and that such a conservative variant can include naturally and non-naturally occurring amino acid analogs.

It is understood that a fragment of a FP receptor variant containing the amino acid sequence of SEQ ID NO: 17, 18, 19, or 20 can be useful in a method of the invention. As non-limiting examples, a functional fragment of a FP receptor variant such as a ligand-binding fragment or a fragment of a FP receptor variant that is involved in signal transduction can be useful in a method of the invention in place of the full-length FP receptor variant. As further understood by one skilled in the art, a FP receptor variant can optionally include non-homologous amino acid sequence. As non-limiting examples, a FP receptor variant can contain an epitope tag or can be fused to a non-homologous polypeptide such as gluthionine S-transferase.

As discussed above, the FP receptor variants VAR-1 through VAR-6 contain amino acid sequence that is not present in the wild-type FP receptor SEQ ID NO: 14 (see FIG. 7). For example, the alternatively spliced FP receptor variants VAR-1, VAR-2, VAR-3, VAR-4 and VAR-6 contain unique carboxy terminal amino acid sequence disclosed herein as SEQ ID NO: 21, 22, 23, 24 or 25, respectively. Furthermore, a nine amino acid sequence spanning the junction between conserved exon 2 and the newly identified exons present in the particular alternatively spliced FP receptor variant from VAR-1/VAR-3, VAR-2, VAR-4, or VAR-6 are disclosed herein as SEQ ID NO: 17, 18, 19 or 20, respectively. These nine amino acid sequences begin with four amino acid residues that correspond to amino acid sequence present in conserved exon 2 and further include five amino acid residues derived from newly identified exons present in a particular alternatively spliced FP receptor variant. Thus, the invention provides an isolated polypeptide containing the amino acid sequence of SEQ ID NO: 17, 18, 19, 20, 21, 22, 23, 24, or 25. The invention further provides an isolated polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. As non-limiting examples, the invention provides an isolated polypeptide containing the amino acid sequence of SEQ ID NO: 2, 4, 6, 8, 10, or 12 such as an isolated polypeptide consisting of the amino acid sequence of SEQ ID NO: 2, 4, 6, 8, 10, or 12.

Further provided herein is an isolated polypeptide containing or consisting of substantially the same amino acid sequence as SEQ ID NO: 2, 4, 6, 8, 10, or 12. The term "substantially the same," when used herein in reference to an amino acid sequence, means a polypeptide having a similar, non-identical sequence that is considered by those skilled in the art to be a functionally equivalent amino acid sequence. An amino acid sequence that is substantially the same as a reference amino acid sequence can have at least 70%, at least 80%, at least 90%, or at least 95% or more identity to the reference sequence. The term substantially the same amino acid sequence also includes sequences encompassing, for example, modified forms of naturally occurring amino acids such as D-stereoisomers, non-naturally occurring amino acids, amino acid analogs and mimetics so long as the polypeptide containing such a sequence retains a functional activity of the reference FP receptor variant. A functional activity of a FP receptor variant of the invention can be, for example, the ability to bind a compounds such as, but not limited to, $PGF_{2\alpha}$, prostamide $F_{2\alpha}$, and $PGF_{2\alpha}$1-glyceryl ester, or the ability to initiate a particular intracellular signal transduction pathway.

It is understood that minor modifications in primary amino acid sequence can result in a polypeptide that has a substantially equivalent function as compared to a polypeptide of the invention. These modifications can be deliberate, as through site-directed mutagenesis, or may be accidental such as through spontaneous mutation. For example, it is understood that only a portion of the entire primary structure of a FP receptor variant can be required in order to bind to a compound such as $PGF_{2\alpha}$, prostamide $F_{2\alpha}$, or $PGF_{2\alpha}1$-glyceryl ester. Moreover, fragments of a FP receptor variant of the invention containing the amino acid sequence of SEQ ID NO: 17, 11, 19, or 20 similarly are included within the definition of substantially the same amino acid sequence as long as at least one biological function of the FP receptor variant is retained. It is understood that various molecules can be attached to a FP receptor variant or other polypeptide of the invention. These molecules include, without limitation, heterologous polypeptides, carbohydrates, lipids, or chemical moieties such as radioactive or fluorescent label moieties.

The invention further provides a FP receptor variant binding agent which binds the amino acid sequence of SEQ ID NO: 21, 22, 23, 24 or 25, or an epitope thereof. As discussed above, each of SEQ ID NO: 21-25 represents the unique carboxy terminal amino acid sequence of an alternatively spliced FP receptor variant. A FP receptor variant binding agent of the invention can be, without limitation, an antibody or antigen binding fragment thereof which binds the amino acid sequence of SEQ ID NO 21, 22, 23, 24 or 25, or an epitope thereof.

As used herein, the term "FP receptor variant binding agent" means a molecule, such as a simple or complex organic molecule, carbohydrate, peptide, peptidomimetic, protein, glycoprotein, lipoprotein, lipid, nucleic acid molecule, antibody, aptamer or the like that specifically binds the unique FP receptor variant carboxy-terminal amino acid sequence disclosed herein as SEQ ID NO: 21, 22, 23, 24 or 25, or an epitope thereof. It is understood that such a binding agent does not specifically bind to a wild-type FP receptor such as SEQ ID NO: 14 since a wild-type FP receptor does not contain the unique carboxy terminal amino acid sequence disclosed herein as SEQ ID NO: 21, 22, 23, 24 or 25.

A FP receptor variant binding agent of the invention can be a polypeptide that specifically binds with high affinity or avidity to SEQ ID NO: 21, 22, 23, 24 or 25 without substantial cross-reactivity to other unrelated sequences. The affinity of a FP receptor variant binding agent of the invention generally is greater than about $10^5$ $M^1$ and can be greater than about $10^6$ $M^{-1}$. A FP receptor variant binding agent of the invention also can bind with high affinity such as an affinity greater than $10^7$ $M^{-1}$ to $10^9$ $M^{-1}$. Specific examples of binding agents of the invention include, but are not limited to, polyclonal and monoclonal antibodies that specifically bind an epitope within SEQ ID NO: 21, 22, 23, 24 or 25; and nucleic acid molecules, nucleic acid analogs, and small organic molecules, identified, for example, by affinity screening of a nucleic acid or small molecule library against SEQ ID NO: 21, 22, 23, 24 or 25. For certain applications, a FP receptor variant binding agent can be utilized that preferentially recognizes a particular conformational or post-translationally modified state of SEQ ID NO: 21, 22, 23, 24 or 25. It is understood that a FP receptor variant binding agent of the invention can be labeled with a detectable moiety, if desired, or rendered detectable by specific binding to a detectable secondary agent.

In one embodiment, a FP receptor variant binding agent of the invention is an antibody or antigen-binding fragment thereof. As used herein, the term "antibody" is used in its broadest sense to mean a polyclonal or monoclonal antibody or an antigen binding fragment of such an antibody. Such an antibody of the invention is characterized by having specific binding activity for SEQ ID NO: 21, 22, 23, 24 or 25, or an epitope thereof, of at least about $1 \times 10^5$ $M^{-1}$. Thus, Fab, $F(ab')_2$, Fd and Fv fragments of an antibody, which retain specific binding activity for SEQ ID NO: 21, 22, 23, 24, or 25, or an epitope thereof, are included within the definition of antibody as used herein. Specific binding activity can be readily determined by one skilled in the art, for example, by comparing the binding activity of the antibody to SEQ ID NO: 21, 22, 23, 24 or 25, versus a control sequence. Methods of preparing polyclonal or monoclonal antibodies are well known to those skilled in the art. See, for example, Harlow and Lane, *Antibodies: A Laboratory Manual*, Cold Spring Harbor Laboratory Press (1988).

It is understood that the term antibody includes naturally occurring antibodies as well as non-naturally occurring antibodies such as, without limitation, single chain antibodies, chimeric, bi-functional and humanized antibodies, and antigen-binding fragments thereof. Such non-naturally occurring antibodies can be constructed using solid phase peptide synthesis, produced recombinantly or obtained, for example, by screening combinatorial libraries consisting of variable heavy chains and variable light chains as described in Huse et al., *Science* 246:1275-1281 (1989). These and other methods of making, for example, chimeric, humanized, CDR-grafted, single chain, and bi-functional antibodies are well known to those skilled in the art (Winter and Harris, *Immunol. Today* 14:243-246 (1993); Ward et al., *Nature* 341:544-546 (1989); Harlow and Lane, supra, 1988; Hilyard et al., *Protein Engineering: A practical approach* (IRL Press 1992); and Borrabeck, *Antibody Engineering*, 2d ed. (Oxford University Press 1995)).

An antibody of the invention can be prepared using as an antigen a polypeptide or peptide containing SEQ ID NO: 21, 22, 23, 24 or 25, or an epitope thereof, which can be prepared, for example, from natural sources, produced recombinantly, or chemically synthesized. Such a polypeptide or peptide is a functional antigen if the polypeptide or peptide can be used to generate an antibody that specifically binds SEQ ID NO: 21, 22, 23, 24 or 25, or an epitope thereof. As is well known in the art, a non-antigenic or weakly antigenic polypeptide or peptide can be made antigenic by coupling the polypeptide or peptide to a carrier molecule such as bovine serum albumin (BSA) or keyhole limpet hemocyanin (KLH). Various other carrier molecules and methods for coupling a polypeptide or peptide to a carrier molecule are well known in the art (see, for example, Harlow and Lane, supra, 1988). An antigenic polypeptide or peptide can also be generated by expressing the polypeptide or peptide as a fusion protein, for example, fused to glutathione S transferase, polyHis or the like. Methods for expressing polypeptide fusions are well known to those skilled in the art as described, for example, in Ausubel et al., *Current Protocols in Molecular Biology* (Supplement 47), John Wiley & Sons, New York (1999).

The present invention also provides a cell that includes an exogenously expressed polypeptide containing the amino acid sequence of SEQ ID NO: 17, 18, 19, 20, 21, 22, 23, 24 or 25. Further provided herein is a cell that includes an exogenously expressed polypeptide containing an amino acid sequence having at least 50% amino acid identity with SEQ ID NO: 14, and the amino acid sequence of SEQ ID NO: 17, 18, 19, 20, 21, 22, 23, 24, or 25, or a conservative variant thereof. The invention provides, for example, a cell that includes an exogenously expressed polypeptide containing the amino acid sequence of SEQ ID NO: 2, 4, 6, 8, 10, or 12.

Such a cell containing an exogenously expressed polypeptide of the invention can be generated by expressing a nucleic acid molecule encoding the polypeptide in a suitable host cell, such as a bacterial cell, yeast cell, oocyte or other amphibian cell, or mammalian cell, using methods well known in the art. Suitable expression vectors are well known in the art and include vectors in which a nucleic acid molecule is operatively linked to a regulatory element such as a promoter or enhancer region that is capable of regulating expression of a linked nucleic acid molecule. Appropriate expression vectors include, without limitation, those that can be replicated in eukaryotic or prokaryotic cells, those that remain episomal as well as those which integrate into the host cell genome, and those including constitutive, inducible or regulated promoters, enhancers or other regulatory elements.

Suitable expression vectors for prokaryotic or eukaryotic cells are well known to those skilled in the art (see, for example, Ausubel et al., supra, 1999). Eukaryotic expression vectors can contain, for example, a regulatory element such as, but not limited to, the SV40 early promoter, the cytomegalovirus (CMV) promoter, the mouse mammary tumor virus (MMTV) steroid-inducible promoter, the Moloney murine leukemia virus (MMLV) promoter, and the like. One skilled in the art will know or can readily determine an appropriate expression vector for a particular host cell.

Useful expression vectors optionally contain a regulatory element that provides cell or tissue specific expression or inducible expression of the operatively linked nucleic acid molecule. One skilled in the art can readily determine an appropriate tissue-specific promoter or enhancer that allows expression of a polypeptide of the invention in a desired tissue. Furthermore, any of a variety of inducible promoters or enhancers can also be included in an expression vector for regulated expression of a polypeptide of the invention. Such inducible systems include, yet are not limited to, a tetracycline inducible gene regulatory region (Gossen & Bijard, Proc. Natl. Acad. Sci. USA, 89:5547-5551 (1992); Gossen et al., Science, 268:1766-1769 (1995); Clontech, Palo Alto, Calif.); a metallothionein promoter inducible by heavy metals; an insect steroid hormone responsive gene regulatory region responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); a mouse mammory tumor virus (MMTV) gene regulatory region induced by steroids such as glucocortocoid and estrogen (Lee et al., Nature, 294:228-232 (1981); and a heat shock promoter.

An expression vector useful in the invention can be a viral vector such as, without limitation, a retrovirus, adenovirus, adeno-associated virus, lentivirus, or herpesvirus vector. Viral based systems provide the advantage of being able to introduce relatively high levels of a heterologous nucleic acid molecule into a variety of cells. Additionally, certain viral vectors can introduce heterologous DNA into non-dividing cells. A variety of suitable viral expression vectors are well known in the art and include, without limitation, herpes simplex virus vectors (U.S. Pat. No. 5,501,979), vaccinia virus vectors (U.S. Pat. No. 5,506,138), cytomegalovirus vectors (U.S. Pat. No. 5,561,063), modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

A cell can be generated that transiently or stably expresses an exogenously expressed polypeptide of the invention. Expression vectors for transient or stable expression of a polypeptide of the invention can be introduced into cells using transfection methods well known to one skilled in the art. Such methods include, without limitation, infection using viral vectors, lipofection, electroporation, particle bombardment and transfection such as calcium-phosphate mediated transfection. Detailed procedures for these methods can be found in Sambrook et al., Molecular Cloning: A Laboratory Manual Cold Spring Harbor Laboratory Press (1989), and the references cited therein. Useful mammalian expression vectors and methods of introducing such vectors into mammalian cells either ex vivo or in vivo are well known in the art. As non-limiting examples, a plasmid expression vector can be introduced into a cell by calcium-phosphate mediated transfection, DEAE dextran-mediated transfection, lipofection, polybrene- or polylysine-mediated transfection, electroporation, or by conjugation to an antibody, gramacidin S, artificial viral envelope or other intracellular carrier. A viral expression vector can be introduced into a cell by infection or transduction, for example, or by encapsulation in a liposome. It further is understood that polypeptides can be delivered directly into cells using a lipid-mediated delivery system (Zelphati et al., J. Biol. Chem. 276:35103-35110 (2001)) to produce a cell that contain exogenously expressed polypeptides of the invention which include FP receptor variants.

Exemplary host cells that can be used to exogenously express a polypeptide of the invention include, yet are not limited to, mammalian primary cells; established mammalian cell lines such as COS, CHO, HeLa, NIH3T3, HEK 293, and HEK 293/EBNA cells; amphibian cells such as Xenopus embryos and oocytes; and other vertebrate cells. Exemplary host cells further include, without limitation, insect cells such as Drosophila, Spodoptera frugiperda and other cells compatible with baculovirus expression systems (Murakimi et al., 2001, Cytokine, 13(1):18-24); yeast cells such as Saccharomyces cerevisiae, Saccharomyces pombe, or Pichia pastoris; and prokaryotic cells such as Escherichia coli. Following transfection, cells exogenously expressing a polypeptide of the invention can be selected, for example, using drug resistance. A quantitative assay such as, for example, immunoblot analysis, immunoprecipitation or ELISA can determine the amount of a polypeptide of the invention expressed in a transfected cell. Such methods are known to one skilled in the art and can be found, for example, in Ausubel et al., supra, 1989, or in Harlow et al., supra, 1988.

Further provided herein are methods for identifying a compound that modulates a FP receptor, identifying a compound that differentially modulates a FP receptor, identifying a compound that specifically binds a FP receptor, and identifying a compound that differentially binds to a FP receptor. In particular, the invention provides a method for identifying a compound that modulates a FP receptor variant by contacting a FP receptor variant with a compound and determining the level of an indicator which correlates with modulation of a FP receptor variant, where an alteration in the level of the indicator as compared to a control level indicates that the compound is a compound that modulates the FP receptor variant. Further provided herein are methods for identifying a compound that modulates a FP receptor variant by contacting an isolated FP receptor variant or a FP receptor variant over-expressed in a genetically engineered cell with a compound and determining the level of an indicator which correlates with modulation of a FP receptor variant, where an alteration in the level of the indicator as compared to a control level indicates that the compound is a compound that modulates the FP receptor variant.

As used herein in reference to a FP receptor variant, the term "modulates" means the ability to alter a characteristic of a FP receptor variant. A characteristic of a FP receptor variant that can be altered can include, without limitation, an amount, activity, or physical conformation of a FP receptor variant. As a non-limiting example, a compound that modulates a FP receptor variant can increase or decrease the binding of a FP receptor variant to a ligand such as $PGF_{2\alpha}$, prostamide $F_{2\alpha}$, or $PGF_\alpha$1-glyceryl ester. Also, for example, a compound can increase or decrease the binding of a FP receptor variant to an intracellular signaling molecule that initiates a signal transduction pathway within a cell. It is understood that compounds that modulate a FP receptor variant include compounds that specifically bind to a FP receptor variant as well as compounds that do not specifically bind to a FP receptor variant.

A method of the invention for identifying a compound that modulates a FP receptor variant involves determining the level of an indicator which correlates with modulation of a FP receptor variant, where an alteration in the level of the indicator as compared to a control level indicates that the compound modulates the FP receptor variant. As used herein, the term "indicator" means a detectable substance which is altered qualitatively or quantitatively in response to modulation of a FP receptor variant. An indicator can be a substance that is normally present in a cell such as a signal transduction molecule, or a substance that is exogenously expressed or otherwise added to a cell the level of which correlates with modulation of a FP receptor variant, such as luciferase. Signal transduction molecules are intracellular substances such as, without limitation, cyclic AMP, inositol phosphates and calcium, the level of which can be altered in response to modulation of a FP receptor variant.

As understood by those of skill in the art, assay methods for identifying compounds that modulate a FP receptor variant generally require comparison to a control. For example, in a method of the invention an alteration in the level of an indicator which correlates with modulation of a FP receptor variant is compared to a control level of the indicator. One type of a control is a sample that is treated substantially the same as the FP receptor variant which is contacted with a compound, with the distinction that the control sample is not exposed to the compound. Controls include, but are not limited to, historical reference values, and samples that are assayed simultaneously or sequentially in comparison to the FP receptor variant which is contacted with a compound.

In one embodiment, a method of the invention is practiced using calcium as the indicator. For example, as disclosed herein in Example III, a FLIPR assay can be used to identify compounds that modulate a FP receptor variant by determining the level of calcium that results after contacting a receptor with a compound. Exogenously expressed substances such as, for example, luciferase, b-galactosidase and green fluorescent protein (GFP) also can be indicators useful in a method of the invention (see Example III).

Further provided herein are methods for identifying a compound that specifically binds to a FP receptor variant by contacting a FP receptor variant with a compound and determining specific binding of the compound to the FP receptor variant. Additionally provided herein are methods for identifying a compound that specifically binds to a FP receptor variant by contacting an isolated FP receptor variant or a FP receptor variant over-expressed in a genetically engineered cell with a compound and determining specific binding of the compound to the FP receptor variant.

As used herein in reference to a compound and a FP receptor variant, the term "specific binding" means binding with an affinity for the target FP receptor variant that is measurably higher than the affinity for an unrelated polypeptide such as an unrelated G protein coupled receptor such as a rhodopsin receptor. For example, a polypeptide or small molecule compound that specifically binds a FP receptor variant has an affinity for the FP receptor variant that is measurably higher than its affinity for an unrelated polypeptide. Binding affinity can be low or high affinity so long as the binding is sufficient to be detectable. For example, a compound can specifically bind a FP receptor variant with a binding affinity (Kd) of about $10^{-4}$ M or less, $10^{-5}$ M or less, $10^{-6}$ M or less, $10^{-7}$ M or less, $10^{-8}$ M or less, or $10^{-9}$ M or less, several methods for detecting or measuring specific binding are well known in the art and discussed further below.

The screening methods of the invention can be practiced using, for example, using a FP receptor variant over-expressed in a genetically engineered cell. As used herein, the term "genetically engineered cell" means a cell having genetic material which is altered by the hand of man. Such a cell can contain a transient or permanent alteration of its genetic material including, for example, alteration in genomic or episomal genetic material. The genetic material in a genetically engineered cell can be altered using, without limitation, an exogenously expressed nucleic acid molecule, chemical mutagen or transposable element. It is understood that a genetically engineered cell can contain one or more man-made alterations, for example, a cell can be co-transfected with more than one expression vector. As used herein in relation to a FP receptor variant in a genetically engineered cell, the term "over-expressed" means having a protein level of a FP receptor variant greater than the level seen in a corresponding non-genetically engineered cell.

As understood by one skilled in the art, a FP receptor variant can be over-expressed in a genetically engineered cell, for example, by exogenously expressing a nucleic acid molecule encoding the FP receptor variant in a cell as described herein above. It is understood that a FP receptor variant can be over-expressed in a cell that does not normally express the FP receptor variant, or in a cell that naturally expresses the endogenous FP receptor variant. As a non-limiting example, a FP receptor variant can be over-expressed in a cell that expresses endogenous FP receptor variant at a low level. In addition, a FP receptor variant can be over-expressed in a genetically engineered cell, for example, by expressing a regulatory molecule in the cell to increase expression of the endogenous FP receptor variant. Another example of a method whereby a FP receptor variant can be over-expressed in a genetically engineered cell is recombination of a heterologous regulatory region such as, without limitation, a promoter, enhancer or 3' regulator, in the cell such that the heterologous regulatory region results in over-expression of endogenous FP receptor variant. As understood by one skilled in the art, over-expression of a FP receptor variant in a genetically engineered cell includes, without limitation, over-expression of the variant on the surface of the cell, within a cell membrane or in the cytosolic portion of the cell.

A FP receptor variant also can be over-expressed in a cell using a chemical agent. Thus, the invention provides a method for identifying a compound that modulates a FP receptor variant by contacting the FP receptor variant with a compound, where the FP receptor variant is over-expressed in a cell using a chemical agent, and determining the level of an indicator which correlates with modulation of a FP receptor variant, where an alteration in the level of the indicator as compared to a control level indicates that the compound is a compound that modulates the FP receptor variant. The invention also provides a method for identifying a compound that specifically binds to a FP receptor variant by contacting the FP receptor variant with a compound, where the FP receptor variant is over-expressed in a cell using a chemical agent, and determining specific binding of the compound to the FP receptor variant. Chemical agents that can result in over-expression of a FP receptor variant can include, without limitation, chemicals that induce the level or activity of regulatory factor, such as a transcription factor, that is involved in FP receptor variant expression.

As described above, the methods of the invention can be practiced with a cell that over-expresses a FP receptor variant. In addition, it is understood that an extract of a cell that over-expresses a FP receptor variant such as a genetically engineered cell that over-expresses a FP receptor variant can be useful in the methods of the invention. Methods for generating different types of cellular extracts including, without limitation, whole cell extracts, membrane extracts, cytosolic extracts and nuclear extracts are well known in the art. As a non-limiting example, receptor enriched plasma membrane fractions can be obtained by continuous or discontinuous gradients of, for example, sucrose as described in Woodward and Lawrence, *Biochemical Pharmacology* 47:1567-1674 (1994).

Isolated FP receptor variants also can be useful in the screening methods of the invention. As used herein in reference to a FP receptor variant, the term "isolated" means the FP receptor variant is substantially separated from other polypeptides. For example, an isolated FP receptor variant derived from a cell can be substantially purified away from other polypeptides in the cell. An isolated FP receptor variant can contain non-polypeptide components, for example, an isolated FP receptor variant can be associated with a natural or artificial lipid containing membrane. In one embodiment, a method of the invention is practiced with a FP receptor variant that contains an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. In another embodiment, a method of the invention is practiced with a FP receptor variant that contains the amino acid sequence of SEQ ID NO: 2, 4, 6, 8, 10, or 12.

A FP receptor variant of the invention can be prepared in isolated form using conventional biochemical purification methods, starting either from tissues containing the desired FP receptor variant or from recombinant sources. A FP receptor variant can be isolated by any of a variety of methods well-known in the art, including, but not limited to, precipitation, gel filtration, ion-exchange, reverse-phase and affinity chromatography, and combinations thereof. Other well-known methods for protein isolation are described in Deutscher et al., *Guide to Protein Purification: Methods in Enzymology Vol.* 182, (Academic Press, (1990)). Methods suitable for isolation of a FP receptor variant of the invention using biochemical purification are known in the art as described for example, in Venter, J. C. and Harrison, L. C. (eds), *Receptor Purification Procedures* (A. R. Liss, (1984)); Litwack, G., *Receptor Purification: Receptors for CNS Agents, Growth Factors, Hormones, & Related Substances,* (Humana Press, (1990)); or Litwack, G., *Receptor Purification: Receptors for Steroid Hormones, Thyroid Hormones, Water Balancing Hormone, & Others,* (Humana Press, (1990)). Purification of the receptor variant can be routinely monitored, for example, by an immunological assay or functional assay such as a binding assay.

An isolated FP receptor variant of the invention also can be produced by chemical synthesis. As a non-limiting example, synthetic isolated FP receptor variants, including fragments thereof, can be produced using an Applied Biosystems, Inc. Model 430A or 431A automatic peptide synthesizer (Foster City, Calif.) employing the chemistry provided by the manufacturer. Methods for synthesizing isolated polypeptides are well known in the art (see, for example, M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis,* (2d ed.), Pierce Chemical Co., Rockford, Ill. (1984)).

In the methods of the invention for identifying a compound that modulates, or specifically binds to, a FP receptor variant, an isolated FP receptor variant or FP receptor variant over-expressed in a genetically engineered cell can be contacted with a compound in a solution under conditions suitable for interaction between the FP receptor variant and compound. Such contact can occur in vivo, such as in a cell, for example in an animal or in cell culture, or in vitro. As used herein, the term "in vitro" means in an artificial environment outside of a living organism or cell. Assays performed in a test tube, microcentrifuge tube, 96 well plate, 384 well plate, 1536 well plate or other assay format outside of an organism or living cell are in vitro assays. Experiments performed in cells or tissues that have been fixed and are therefore dead (sometimes referred to as in situ experiments) or using cell-free extracts from cells are in vitro.

Conditions suitable for contacting an isolated FP receptor variant or FP receptor variant over-expressed in a genetically engineered cell with a compound are dependent on the characteristics of the FP receptor variant and the compound. For example, the overall charge of the FP receptor variant and the compound can be considered when adjusting the salt concentration or pH of a buffering solution to optimize the specific binding or modulation of the FP receptor variant by the compound. Usually a salt concentration and pH in the physiological range, for example, about 100 mM KCl and pH 7.0 are reasonable starting points. In addition, other components such as glycerol or protease inhibitors can be added to the solution, for example, to inhibit polypeptide degradation. It is understood that the stability of the contact between the FP receptor variant and the compound can be effected by the temperature at which such contact occurs and that the optimal temperature for contact can be routinely determined by those skilled in the art. For example, reactions can be performed on ice (4° C.), at room temperature (about 25° C.) or at body temperature (37° C.). Suitable conditions can be similar or identical to conditions used for binding of a compound to the wild-type human FP receptor. Such conditions are known in the art and include, for example, contact in a binding buffer containing 10 mM MES/KOH (pH 6.0), 0.4 mM EDTA, and 10 mM $MnCl_2$, and incubation at room temperature for one hour, as described in Abramovitz et al., supra, 1994.

The screening methods of the invention are useful for identifying compounds that modulate or differentially modulate, or that specifically or differentially bind a FP receptor variant. As used herein, the term "compound" means a molecule of natural or synthetic origin. A compound can be, without limitation, a small organic or inorganic molecule, polypeptide, peptide, peptidomimetic, non-peptidyl compound, carbohydrate, lipid, antibody or antibody fragment, aptamer, or nucleic acid molecule. In one embodiment, the compound is a small organic molecule. It is understood that a compound can have a known or unknown structure, and can be assayed as an isolated molecule or as part of a population of compounds such as a library.

As understood by one skilled in the art, a compound can specifically bind to a FP receptor variant without modulating the FP receptor variant; specifically bind to a FP receptor variant, thereby modulating the FP receptor variant; or modulate a FP receptor variant without specifically binding the FP receptor variant. Compounds that specifically bind to a FP receptor variant can include, without limiation, $PGF_{2\alpha}$ and prostanoid-like compounds. A compound that modulates a FP receptor variant but does not directly bind to the FP receptor variant can be, for example, a compound that binds to or effects the activity of a polypeptide in a cell, where that polypeptide increases or decreases the level of a FP receptor variant. Such polypeptides include, without limitation, transcription or translation regulatory factors, signal transduction polypeptides; kinases and phosphatases; polypeptides that bind to a FP receptor variant; and anti-sense oligonucleotides, inhibitor RNA molecules and ribozymes, which act on the nucleic acid that encodes the FP receptor variant.

Compounds that modulate or specifically bind to a FP receptor variant further include, but are not limited to, agonists and antagonists. An agonist can be a compound that binds to a receptor and activates it, producing a pharmacological response such as contraction, relaxation, secretion, or enzyme activation. An antagonist is a compound which can attenuate the effect of an agonist. An antagonist can be competitive, meaning it binds reversibly to a region of the receptor in common with an agonist, but occupies the site without activating the effector mechanism. The effects of a competitive antagonist can be overcome by increasing the concentration of agonist, thereby shifting the equilibrium and increasing the proportion of receptors occupied by agonist. Alternatively, antagonists can be non-competitive, where no amount of agonist can completely overcome the inhibition once it has been established. Non-competitive antagonists can bind covalently to the agonist binding site (called competitive irreversible antagonists), in which case there is a period before the covalent bond forms during which competing ligands can prevent the inhibition. Other types of non-competitive antagonists act allosterically at a different site on the receptor.

Other classes of compounds that can modulate or specifically bind to a FP receptor variant include inverse agonists, which are compounds which produce an opposite physiological effect to that of an agonist, yet act at the same receptor. Such compounds have also been described as negative antagonists, or as having negative efficacy. Another class of compounds that can modulate or specifically bind to a FP receptor variant is a partial agonist, which is an agonist that is unable to produce maximal activation of the receptor.

A library of compounds can be useful in the screening methods of the invention. Such a library can be a random collection of compounds or a focused collection of compounds, for example, compounds that are rationally designed or pre-selected based on physical or functional characteristics. For example, a library of prostanoids or prostanoid-related compounds can be useful in the screening methods of the invention. Libraries useful in the methods of the invention include, yet are not limited to, natural product libraries derived from, without limitation, microorganisms, animals, plants, and marine organisms; combinatorial chemical or other chemical libraries such as those containing randomly synthesized compounds; combinatorial libraries containing structural analogs of prostanoids or other known compounds, or random or biased assortments of, for example, small organic molecules, polypeptides, oligonucleotides, and combinations thereof. Still other libraries of interest include peptidomimetic, multiparallel synthetic collection, and recombinatorial libraries. Combinatorial and other chemical libraries are known in the art, as described, for example, in Myers, *Curr. Opin. Biotechnol.* 8:701-707 (1997). Appropriate libraries can be assembled from catalog sources such as Cayman Chemical Co. (Ann Arbor, Mich.), BIOMOL Research Laboratories, Inc. (Plymouth Meeting, Pa.), Tocris Cooksoon Inc. (Ellisville, Mo.), and others. These libraries can include, without limitation, fatty acids, fatty acid amides and esters, and eicosanoids.

In a screening method of the invention, the members of a library of compounds can be assayed for activity individually, in pools, or en masse. An example of en masse screening to identify a compound that modulates or specifically binds to a FP receptor variant is as follows: a library of compounds is assayed in pools for the ability to modulate or specifically bind a FP receptor variant; the sub-population which modulates or specifically binds the FP receptor variant is subdivided; and the assay is repeated as needed in order to isolate an individual compound or compounds from the library that modulate or specifically bind the FP receptor variant.

The methods of the invention can utilize high throughput screening (HTS) techniques to identify compounds that modulate or specifically bind to a FP receptor variant. HTS assays permit screening of large numbers of compounds in an efficient manner. Cell-based high throughput screening systems include, but are not limited to, melanophore assays, yeast-based assay systems, and mammalian cell expression systems (Jayawickreme and Kost, *Curr. Opin. Biotechnol.* 8:629-634 (1997)). Automated and miniaturized high throughput screening assays are also useful in the methods of the invention (Houston and Banks, *Curr. Opin. Biotechnol.* 8:734-740 (1997)). High throughput screening assays are designed to identify "hits" or "lead compounds" having the desired modulating or specific binding activity, from which modified compounds can be prepared to improve a property of the initial lead compound. Chemical modification of the "hit" or "lead compound" can be based on an identifiable structure/activity relationship (SAR) between the "hit" and a FP receptor variant of the invention. It is understood that assays such as the melanophore and radioligand binding assays disclosed below, and the FLIPR and luciferase assays disclosed in Example III, can be performed as conventional or high through-put screening assays to identify a compound that modulates or specifically binds to a FP receptor variant according to a method of the invention.

Various types of assays can be useful for identifying a compound that modulates or specifically binds to a FP receptor variant in a method of the invention. For example, several assays can be used to measure specific binding of a compound to a FP receptor variant in a method of the invention. A classic assay used for measuring specific binding of a compound to a receptor is a radioligand binding assay. Radioligand binding assays can be performed on cells or in solution, for example, using isolated cell membranes. As a non-limiting example, cells or cell membranes that transiently or stably over-express a FP receptor variant can be incubated with a ligand including a novel or known ligand such as radioactively labeled $PGF_{2\alpha}$. After washing away any unbound radioactively labeled $PGF_{2\alpha}$, compounds of interest can be incubated with the cells. After incubation, the solution around the cells is collected and the amount of radioactively labeled $PGF_{2\alpha}$ in the solution is determined using, for example, a scintillation counter. Compounds that specifically bind to the FP receptor variant displace radioactively labeled $PGF_{2\alpha}$ from the receptor and thereby increase radioactively labeled $PGF_{2\alpha}$ in the solution. A method for a whole cell radioligand binding assay using $PGF_{2\alpha}$ is described, for example, in Fujino et al., *J. Biol. Chem.* 275:29907-29914 (2000). As understood by one skilled in the art, a ligand such as $PGF_{2\alpha}$ also can be labeled with a non-radioactive moiety such as a fluorescent moiety can be used for labeling.

A variety of other assays well known in the art can be used to determine specific binding of a compound to a FP receptor variant in a method of the invention. Such methods for detecting a FP receptor variant in contact with a compound include, without limitation, detecting specific binding of a labeled compound to a FP receptor variant which is immobilized. For example, a compound can be conjugated to a radiolabel, fluorescent label or enzyme label such as alkaline phosphatase, horse radish peroxidase or luciferase. Labeled compound can then bind to a FP receptor variant, for example a FP receptor variant membrane preparation, which is immobilized, for example, on a solid support such as a latex bead. Unbound compound is washed away, and the amount of specifically bound compound can be detected based on its label. Fluorescently labeled compound can also be bound to a FP receptor variant in solution and bound complexes detected, for example using a fluorescence polarization assay (Degterev et al., *Nature Cell Biology* 3:173-182 (2001)). Such assays also can be performed where the FP receptor variant is labeled and the compound is immobilized or in solution. One skilled in the art understands that a variety of additional means can be used to determine specific binding to a FP receptor variant; as non-limiting examples, binding of a compound to a $^{15}$N-labeled FP receptor variant can be detected using nuclear magnetic resonance (NMR), or specific binding can be determined using an antibody that specifically recognizes a ligand-bound FP receptor variant.

High-throughput assays for determining specific binding to a FP receptor variant further include, but are not limited to, scintillation proximity assays (Alouani, *Methods Mol. Biol.* 138:135-41 (2000)). Scintillation proximity assays involve the use of a fluomicrosphere coated with an acceptor molecule, such as an antibody, to which an antigen will bind selectively in a reversible manner. For example, a compound can be bound to a fluomicrosphere using an antibody that specifically binds to the compound, and contacted with a $^3$H or $^{125}$I labeled FP receptor variant. If the labeled FP receptor variant specifically binds to the compound, the radiation energy from the labeled FP receptor variant is absorbed by the fluomicrosphere, thereby producing light which is easily measured. Such assays can also be performed where the FP receptor variant is bound to the fluomicrosphere and the compound is labeled.

Additional assays suitable for determining specific binding of a compound to a FP receptor variant in a screening method of the invention include, without limitation, UV or chemical cross-linking assays (Fancy, *Curr. Opin. Chem. Biol.* 4:28-33 (2000)) and biomolecular interaction analyses (Weinberger et al., *Pharmacogenomics* 1:395-416 (2000)). Specific binding of a compound to a FP receptor variant can be determined by cross-linking these two components, if they are in contact with each other, using UV or a chemical cross-linking agent. In addition, a biomolecular interaction analysis (BIA) can detect whether two components are in contact with each other. In such an assay, one component, such as a FP receptor variant, for example, a membrane preparation containing a FP receptor variant, is bound to a BIA chip, and a second component such as a compound is passed over the chip. If the two components specifically bind, the contact results in an electrical signal, which is readily detected.

In addition, virtual computational methods and the like can be used to identify compounds that modulate or specifically bind to a FP receptor variant in a screening method of the invention. Exemplary virtual computational methodology involves virtual docking of small-molecule compounds on a virtual representation of a FP receptor variant structure in order to determine or predict specific binding. See, for example, Shukur et al., supra, 1996; Lengauer et al., *Current Opinions in Structural Biology* 6:402-406 (1996); Choichet et al., *Journal of Molecular Biology* 221:327-346 (1991); Cherfils et al., *Proteins* 11:271-280 (1991); Palma et al., *Proteins* 39:372-384 (2000); Eckert et al., *Cell* 99:103-115 (1999); Loo et al., *Med. Res. Rev.* 19:307-319 (1999); Kramer et al., *J. Biol. Chem.* (2000).

One type of assay that does not directly measure binding to a FP receptor variant, but measures activation of a signal transduction pathway, is an assay based on melanophores, which are skin cells that provide pigmentation to an organism (Lerner, *Trends Neurosci.* 17:142-146 (1994)). In numerous animals, including fish, lizards and amphibians, melanophores are used, for example, for camouflage. The color of the melanophore is dependent on the intracellular position of melanin-containing organelles, termed melanosomes. Melanosomes move along a microtubule network and are clustered to give a light color or dispersed to give a dark color. The distribution of melanosomes is regulated by G protein coupled receptors and cellular signaling events, where increased concentrations of second messengers such as cyclic AMP and diacylglycerol result in melanosome dispersion and darkening of melanophores. Conversely, decreased concentrations of cyclic AMP and diacylglycerol result in melanosome aggregation and lightening of melanophores.

A melanophore-based assay can be advantageously used to identify a compound that modulates or specifically binds to a FP receptor variant, due to the regulation of melanosome distribution by FP receptor variant-stimulated intracellular signaling. For example, a FP receptor variant can be overexpressed in genetically engineered melanophore cells, for example, frog melanophore cells. Compounds that modulate or specifically bind to the FP receptor variant can stimulate or inhibit G protein coupled receptor signaling. Both stimulation or inhibition of signaling can be determined since the system can be used to detect both aggregation of melanosomes and lightening of cells, and dispersion of melanosomes and darkening of cells. Thus, the color of the cells, determined by the level of melanin in the cells, is an indicator that can be used to identify a compound that modulates or specifically binds to a FP receptor variant in a method of the invention.

In addition to the methods described above for identifying a compound that modulates or specifically binds a FP receptor variant, the invention also provides related methods for identifying a compound that differentially modulates or differentially binds to a FP receptor variant. It is understood that the FP receptor variants, cells, compounds, indicators, conditions for contacting, and assays, described above also can be applied to methods for identifying a compound that differentially modulates or differentially binds to a FP receptor variant.

Provided herein is a method for identifying a compound that differentially modulates a FP receptor variant by a) contacting an isolated FP receptor variant or a FP receptor variant over-expressed in a genetically engineered cell with a compound; b) determining the level of an indicator which correlates with modulation of a FP receptor variant; c) contacting a second receptor with the compound; d) determining the level of a corresponding indicator after contacting of the compound to the second receptor; and e) comparing the level of the indicator from step (b) with the level of the corresponding indicator from step (d), where a different level of the indicator from step (b) compared to the level of the corresponding indicator from step (d) indicates that the compound is a compound that differentially modulates the FP receptor variant.

As described above, an indicator is a detectable substance which is altered qualitatively or quantitatively in response to modulation of a FP receptor variant. A "corresponding indicator" is an indicator that can be compared to the indicator which correlates with modulation of the FP receptor variant in step (b). For example, a corresponding indicator can be the same indicator as the indicator which correlates with modulation of the FP receptor variant in step (b). In addition, for example, a corresponding indicator can be a different indicator as the indicator which correlates with modulation of the FP receptor variant in step (b) so long as the corresponding indicator can be compared to the indicator which correlates with modulation of the FP receptor variant in step (b). As a non-limiting example, the indicator in step (b) can be calcium and the corresponding indicator can be a substance whose amount is directly correlated with calcium level, such as a signal transduction molecule. As a further non-limiting example, the indicator in step (b) and corresponding indicator in step (d) can be related molecules, such as two different fluorophores. In one embodiment, the level of the indicator which correlates with modulation of the FP receptor variant in step (b) is greater than the level of the corresponding indicator from step (d). In another embodiment, the level of the indicator which correlates with modulation of the FP receptor variant in step (b) is less than the level of the corresponding indicator from step (d).

The invention also provides a method for identifying a compound that differentially binds to a FP receptor variant by a) contacting an isolated FP receptor variant or a FP receptor variant over-expressed in a genetically engineered cell with a compound; b) determining specific binding of the compound to the FP receptor variant; c) contacting a second receptor with the compound; d) determining specific binding of the compound to the second receptor; and e) comparing the level of specific binding from step (b) with the level of specific binding from step (d), where a different level of specific binding from step (b) compared to the level of specific binding from step (d) indicates that the compound is a compound that differentially binds to the FP receptor variant. In one embodiment, the different level of specific binding is an increased level of binding. In another embodiment, the different level of specific binding is a decreased level of binding.

As described for the methods of the invention for identifying a compound that modulates or specifically binds a FP receptor variant, the FP receptor variant in step (a) can be any of a variety of FP receptor variants such as an isolated polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof; or an isolated polypeptide containing the amino acid sequence of SEQ ID NO: 2, 4, 6, 8, 10, or 12. In addition, the FP receptor variant can be over-expressed in a genetically engineered cell. For example, the FP receptor variant can be exogenously over-expressed in a genetically engineered cell.

In the methods of the invention for identifying a compound that differentially modulates or differentially binds a FP receptor variant, the second receptor can be any receptor of interest. For example, the second receptor can be a G-protein coupled receptor such as, without limitation, any other FP receptor such as a different FP receptor variant or a wild-type FP receptor. In addition, for example, the second receptor can contain the amino acid sequence SEQ ID NO: 14, or a functional fragment thereof. The second receptor can be, for example, expressed in a cell endogenously or exogenously or can be an isolated receptor polypeptide.

It is understood that the methods of the invention can be practiced where the FP receptor variant and second receptor are expressed, for example, in different cells. In addition, the methods of the invention can be practiced where the FP receptor variant and second receptor are expressed in the same cell, for example, where the FP receptor variant does not have identical binding and signal transduction effects as the co-expressed second receptor.

The invention further provides an isolated nucleic acid molecule having a nucleotide sequence that encodes a polypeptide containing an amino acid sequence having at least 50% amino acid identity with SEQ ID NO: 14 and the amino acid sequence of SEQ ID NO: 17, 18, 19, or 20, or a conservative variant thereof. The invention also provides an isolated nucleic acid molecule containing a nucleotide sequence that encodes the amino acid sequence of SEQ ID NO: 2, 4, 6, 8, 10, or 12. Such a nucleotide sequence can be, without limitation, SEQ ID NO: 1, 3, 5, 7, 9, or 11.

Isolated nucleic acid molecules include DNA and RNA molecules as well as both sense or complementary antisense strands. It is understood that an isolated nucleic acid molecule of the invention can be a double-stranded or single-stranded molecule, an RNA or DNA molecule, and can optionally include noncoding sequence. DNA molecules of the invention include cDNA sequences as well as wholly or partially chemically synthesized DNA sequences.

The nucleic acid molecules of the invention optionally include heterologous nucleic acid sequences that are not part of the FP receptor variant-encoding sequences in nature. Such a heterologous nucleic acid sequence can be optionally separated from the FP receptor variant-encoding sequence by an encoded cleavage site that facilitates removal of non-FP receptor variant polypeptide sequences from the expressed fusion protein. Heterologous nucleic acid sequences include, without limitation, sequences encoding poly-histidine sequences, FLAG tags and other epitopes, and glutathione-S-transferase, thioredoxin, and maltose binding protein domains or other domains or sequences that facilitate purification or detection of the fusion protein containing a FP receptor variant of the invention.

An isolated nucleic acid molecule of the invention contains nucleotide sequence that is distinct from the nucleotide sequence in the human FP receptor genomic clone AL136324.6 since the nucleotide sequence which encodes the amino acid sequence SEQ ID NO: 17, 18, 19, or 20 spans the junction between conserved exon 2 and the newly identified alternatively spliced exons. The intron/exon structure of the human FP receptor genomic clone AL136324.6 is shown in FIG. 8. As understood by one skilled in the art, an intron starts with the dinucleotide GT and ends with the dinucleotide AG.

The location of exons from the human FP receptor genomic clone AL136324.6 that are present in alternatively spliced human FP receptor variants VAR-1 to VAR-6 as determined using BLAST searches are as follows: FP receptor variant VAR-1 alternatively spliced sequence corresponds to human genomic clone AL136324.6 at a range from +64861 to +64938; FP receptor variant VAR-2 alternatively spliced sequence corresponds to human genomic clone AL136324.6 at a range from +70926 to +71071; FP receptor variant VAR-3 alternatively spliced sequence corresponds to human genomic clone AL136324.6 at a range from +64861 to +64936 and +70986 to +71071; FP receptor variant VAR-4 alternatively spliced sequence corresponds to human genomic clone AL136324.6 at a range from +81522 to +81620; FP receptor variant VAR-5 alternatively spliced sequence corresponds to human genomic clone AL136324.6 at a range from +99204 to +99347; and FP receptor variant VAR-6 alternatively spliced sequence corresponds to human genomic clone AL136324.6 at a range from +98016 to +98123 and +99204 to +99347.

It is understood that a nucleic acid of the invention such as FP receptor variant VAR-4 does not encompass any of the following human EST clones listed as follows: BG220560, BG19713, BG208551, BG 209077, BG 199710, BG 196146, BG 218035.

The invention further provides a vector containing a nucleic acid molecule having a nucleotide sequence that encodes a polypeptide containing an amino acid sequence having at least 50% amino acid identity with SEQ ID NO: 14 and the amino acid sequence of SEQ ID NO: 17, 18, 19, 20, 21, 22, 23, 24, or 25, or a conservative variant thereof. The invention also provides a vector containing a nucleic acid molecule containing a nucleotide sequence that encodes the amino acid sequence of SEQ ID NO: 2, 4, 6, 8, 10, or 12. For example, such a vector can contain a nucleic acid molecule having the nucleotide sequence of SEQ ID NO: 1, 3, 5, 7, 9, or 11. The invention further provides a host cell including a vector which contains a nucleic acid molecule of the invention.

Vectors are useful, for example, for subcloning and amplifying a nucleic acid molecule encoding a polypeptide of the invention and for recombinantly expressing the encoded FP variant receptor or other polypeptide. Vectors of the invention include, without limitation, viral vectors such as a bacteriophage, baculovirus and retrovirus vectors; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. Vectors further encompass expression vectors such as those discussed herein above.

The invention also provides an isolated nucleic acid molecule containing a nucleotide sequence that encodes the amino acid sequence of SEQ ID NO: 17, 18, 19, or 20. Such a nucleic acid molecule of the invention can be used, without limitation, in recombinant cloning methods or as a nucleic acid probe. The amino acid sequence of SEQ ID NO: 17, 18, 19, and 20 each contains nine amino acids which begin with four amino acid residues that correspond to the amino acid sequence present in conserved exon 2 and further include five amino acid residues derived from newly identified exons present in a particular alternatively spliced FP receptor variant.

As non-limiting examples, nucleic acid molecules of the invention can be derived from the unique nucleotide sequence which surrounds the junction between conserved exon 2 and the newly identified alternatively spliced exons present in FP receptor variants VAR-1 to VAR-6. For example, nucleic acid molecules containing 20 nucleotides spanning the splice junction are as follows. The FP receptor variants VAR-1 and VAR-3 include the nucleic acid sequence ccatttctggggatacagaat (SEQ ID NO: 26) at the 5' splice junction and FP receptor variant VAR-1 contains the nucleic acid sequence cttacataggttacaatggc (SEQ ID NO: 27) at the 3' splice junction. The FP receptor variant VAR-2 includes the nucleic acid sequence cccatttctgaaaatagaag (SEQ ID NO: 28) at the 5' splice junction, while the FP receptor variants VAR-2 and VAR-3 include the nucleic acid sequence tgttggaaaggttacaatgg (SEQ ID NO: 29) at the 3' splice junction. FP receptor variant VAR-4 contains the nucleic acid sequence ccatttctggtgaaagaaac (SEQ ID NO: 30) at the 5' splice junction. Furthermore, FP receptor variant VAR-4 has the nucleic acid sequence ttttgaaatgttacaatggc (SEQ ID NO: 31) at the 3' splice junction, and FP receptor variant VAR-5 includes the nucleic acid sequence cccatttctgcgataagaca (SEQ ID NO: 32) at the 5' splice junction. The FP receptor variants VAR-5 and VAR-6 include the nucleic acid sequence atgccgtcaagttacaatgg (SEQ ID NO: 33) at their 3' splice junction, and FP receptor variant FP-6 includes the nucleic acid sequence cccatttctgacacattggg (SEQ ID NO: 34) at the 5' splice junction.

As understood by one skilled in the art, a nucleic acid molecule of the invention can contain nucleotide sequence in addition to the nucleotide sequence of SEQ ID NO: 26, 27, 28, 29, 30, 31, 32, 33, or 34. For example, a nucleic acid molecule of the invention can contain further naturally occurring sequence at the 5' or 3' end of SEQ ID NO: 26, 27, 28, 29, 30, 31, 32, 33, or 34. Also, for example, a nucleic acid molecule of the invention can include additional heterologous sequences such as nucleotide sequences encoding restriction enzyme sites or epitope tags. As non-limiting examples, nucleic acid molecules of the invention can be used in hybridization reactions such as Southern and Northern blots, to encode polypeptide sequence in recombinant cloning methods, or as primers in polymerase chain reactions.

The invention also provides an isolated nucleic acid molecule having a nucleotide sequence that encodes a polypeptide containing or consisting of substantially the same amino acid sequence as SEQ ID NO: 2, 4, 6, 8, 10, or 12 as described further above. For example, the invention provides an isolated nucleic acid molecule having a nucleotide sequence of SEQ ID NO:1, 3, 5, 7, 9, or 11.

The invention further provides a method for preventing or reducing the severity of a disease associated with a FP receptor or FP receptor variant in a subject by introducing into the subject a compound that modulates or specifically binds to a FP receptor variant or another compound identified by a method of the invention. The invention also provides a method for regulating muscle contraction in a subject by introducing into the subject a compound that modulates or specifically binds to a FP receptor variant or another compound identified by a method of the invention. In addition, the invention provides a method for preventing or reducing the severity of ocular hypertension in a subject by introducing into the subject a compound that modulates or specifically binds to a FP receptor variant or another compound identified by a method of the invention. Such a compound can be used, without limitation, to prevent or reduce the severity of glaucoma.

As used herein, a "disease associated with a FP receptor or FP receptor variant" means any disease or condition in which modulation of the activity of the wild-type FP receptor or FP receptor variant can be beneficial. It is understood that the underlying cause of the disease may or may not be due to an abnormality in expression or activity of a wild-type FP receptor or FP receptor variant.

A disease associated with a FP receptor or FP receptor variant can be, without limitation, a cardiovascular disorder or an ocular disorder such as glaucoma or ocular hypertension. In addition, a disease associated with a FP receptor or FP receptor variant can be a condition. For example, a compound identified by the methods of the invention which modulate a FP receptor variant can be used, without limitation, to modulate the female reproductive cycle or activity, for example, to induce labor, terminate pregnancy or regulate the female menstrual cycle. As a non-limiting example, such a compound can be used to regulate oestrus in animals.

A compound identified by the methods of the invention can be used, without limitation, to prevent or reduce the severity of glaucoma. Glaucoma, the second most common cause of blindness in the United States, affects about two million Americans, but roughly half are unaware of it. This group of disorders is characterized by progressive damage to the eye at least partly due to intraocular pressure. Normal intraocular pressure (IOP) ranges between 11 and 21 mm Hg; however, this level may not necessarily be healthy for all people. Some people with normal pressure develop optic nerve injury (normal- or low-pressure glaucoma). In contrast, many people have pressure >21 mm Hg without any optic nerve injury (ocular hypertension). Of those with ocular hypertension, only about 1% per year will develop glaucoma.

Glaucoma can be described according to the mechanism of outflow obstruction as either open-angle or closed-angle (angle-closure) glaucoma. Alternatively, classification can be based on etiology as primary or secondary. The primary (conventional) outflow system of the eye is located in the anterior chamber angle and accounts for 83 to 96% of aqueous outflow in human eyes under normal circumstances. The primary outflow system refers to aqueous outflow through the trabecular meshwork, canal of Schlemm, intrascleral channels, and episcleral and conjunctival veins. In open-angle glaucoma with elevated intraocular pressure, pressure elevation occurs because outflow is inadequate despite an angle that appears open and relatively normal on gonioscopic examination. In closed-angle glaucoma, elevated intraocular pressure occurs when normal drainage of aqueous fluid from the eye is sufficiently prevented by a physical obstruction of the peripheral iris. The secondary (alternative) aqueous outflow pathways (known as the unconventional or uveoscleral aqueous outflow system) account for 5 to 15% of the total aqueous outflow. The secondary aqueous outflow pathway refers to aqueous exiting the eye through the anterior face of the ciliary body and percolating through the ciliary muscles to the suprachoroidal space (i.e., between the choroid and sclera), where it eventually exits the eye via scleral channels. It is understood that compounds that modulate or specifically bind to a FP receptor variant or that are otherwise identified according to a method of the invention can be used to treat any of a variety of forms of glaucoma including, but not limited to, normal- or low-pressure glaucoma, glaucoma with elevated intraocular pressure, primary glaucoma and secondary glaucoma.

Furthermore, a compound that modulates or specifically binds to a FP receptor variant or which is otherwise identified by a method of the invention can be used alone or in combination with one or more different compounds or other therapeutics or procedures for treatment of glaucoma. Compounds that are currently used in the treatment of glaucoma include, but are not limited to, topical-blockers such as timolol, levobunolol, carteolol, metipranolol and betaxolol; topical nonselective adrenergic agonists such as epinephrine and dipivefrin; adrenergic agonists such as apraclonidine and brimonidine; topical cholinergic agonists such as pilocarpine and phospholine; oral carbonic anhydrase inhibitors such as acetazolamide and methazolamide; topical carbonic anhydrase inhibitors such as dorzolamide; and topical prostaglandin analogs such as latanoprost, unoprostone, and travoprost.

In the methods of the invention for preventing or reducing the severity of glaucoma or another disease associated with a FP receptor or FP receptor variant, a compound can optionally be formulated together with a pharmaceutically acceptable carrier for delivery to the subject to be treated. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable agent that acts, for example, to stabilize or increase solubility of a pharmaceutical composition. Such a physiologically acceptable agent can be, for example, a carbohydrate such as glucose, sucrose or dextrans; an antioxidant such as ascorbic acid or glutathione; a chelating agent; a low molecular weight polypeptide; or another stabilizer or excipient. Pharmaceutically acceptable carriers including solvents, stabilizers, solubilizers and preservatives, are well known in the art as described, for example, in Martin, *Remington's Pharm. Sci.,* 15th Ed. (Mack Publ. Co., Easton, 1975).

Those skilled in the art can formulate a compound that modulates, differentially modulates, specifically binds, or differentially binds a FP receptor variant to ensure proper compound distribution and bioavailablility in vivo. For example, some regions of the eye can be inaccessible to some systemically administered drugs, and as a result topical drug delivery can be used. Polymers can be added to ophthalmic solutions to increase bioavailability (Ludwig and Ootenhgm, *S.T.P. Pharm. Sci.,* 2:81-87 (1992)). In addition, colloidal systems such as, without limitation, liposomes, microparticles or nanoparticles can be used to increase penetration of a compound into the eye. Ocular drug absorption also can be enhanced using, for example, iontophoresis, prodrugs, and cyclodextrins.

Methods of ensuring appropriate distribution in vivo also can be provided by rechargeable or biodegradable devices, particularly where concentration gradients or continuous delivery is desired. Various slow release polymeric devices are known in the art for the controlled delivery of drugs, and include both biodegradable and non-degradable polymers and hydrogels. Polymeric device inserts can allow for accurate dosing, reduced systemic absorption and in some cases, better patient compliance resulting from a reduced frequency of administration. Those skilled in the art understand that the choice of the pharmaceutical formulation and the appropriate preparation of the compound will depend on the intended use and mode of administration.

A compound that modulates or specifically binds to a FP receptor variant, or that is otherwise identified by a screening method of the invention can be administered to a subject by any effective route. Suitable routes of administration include, but are not limited to, oral, topical, intraocular, intradermal, parenteral, intranasal, intravenous, intramuscular, intraspinal, intracerebral and subcutaneous routes. The present invention also provides compounds containing an acceptable carrier such as any of the standard pharmaceutical carriers, including phosphate buffered saline solution, water and emulsions such as an oil and water emulsion, and various types of wetting agents.

An effective dose of a compound for use in a method of the invention can be determined, for example, by extrapolation from the concentration required in a FP receptor or FP receptor variant binding or activity assay such as one of the assays disclosed herein above. An effective dose of a compound for the treatment of a disease associated with a FP receptor or FP receptor variant also can be determined from appropriate animal models, such as transgenic mice. As a non-limiting example, animal models for pathologies such as glaucoma are well-known in the art. An effective dose for preventing or reducing the severity of a disease is a dose that results in either partial or complete alleviation of at least one symptom of the disease. The appropriate dose of a compound for treatment of a human subject can be determined by those skilled in the art, and is dependent, for example, on the particular disease being treated, nature and bioactivity of the particular compound, the desired route of administration, the gender, age and health of the individual, and the number of doses and duration of treatment.

All journal article, reference and patent citations provided herein, including referenced sequence accession numbers of nucleotide and amino acid sequences contained in various databases, in parentheses or otherwise, whether previously stated or not, are incorporated herein by reference in their entirety.

It is understood that modifications which do not substantially affect the activity of the various embodiments of this invention are also included within the definition of the invention provided herein. Accordingly, the following examples are intended to illustrate but not limit the present invention.

EXAMPLE I

Identification of Alternatively Spliced FP Receptor Variants

This example shows the molecular cloning of several alternatively spliced FP receptor variants and their expression in cell culture.

Total RNA derived from human heart, brain, lung, spleen, small intestine, skeletal muscle, kidney and liver tissue were purchased from Clontech. Total RNA was isolated from human eyes (NDRI; Philadelphia, Pa.) and human ocular tissues (ciliary smooth muscles, trabecular meshwork, ODM-2) using a Qiagen total RNA isolation kit, according to the manufacturer's instructions. The ODM-2 cell line is derived from human non-pigmented ciliary epithelial cells (Escribano et al., *J. Cell. Physiol.* 160:511-521 (1994)). Using 5 mg of human total RNA, first strand cDNA was synthesized using Superscript II RNase H reverse transcriptase (Life Technologies; Carlsbad, Calif.). Reactions (20 µl) containing 5 µg of RNA, 250 ng of oligo (dT), and 100 units of reverse transcriptase were incubated at 42° C. for 1 hour and terminated by incubation at 100° C. for 3 minutes. The PCR buffer contained 10 mM Tris-HCl, pH 8.3, 50 mM KCl, 2 mM MgCl, 2.5 units AmpliTaq DNA polymerase, 0.2 µM upstream and downstream primers, in a final volume of 50 µl. After an initial incubation for 5 minutes at 94° C., samples were subjected to 30 cycles of 30 seconds at 95° C., 30 seconds at 58° C., and 30 seconds at 72° C. in a PE 9700 thermal cycler. The primers used for the detection of alternatively spliced FP receptor variants were as follows:

```
                                               (SEQ ID NO: 15)
     Human FP Forward: TGCAATGCAATCACAGGAAT and (SEQ ID NO: 16)
     Human FP Reverse: CACTCCACAGCATTGACTGG
```

The PCR products were isolated from a 1.5% lower melting agarose gel, and subcloned into the TOPO PCRII vector (Invitrogen; Carlsbad, Calif.). Nucleotide sequencing of the vectors was performed by Sequetech (Mountain View, Calif.).

Full length cDNAs for FP receptor variants VAR-1 to VAR-6 were isolated and subcloned into TOPO pcDNA3.1 PCR cloning vector (Invitrogen; Carlsbad, Calif.) or pCEP4 expression vector (Invitrogen) to create Alt FP/pcDNA3.1 plasmids or Alt FP/pCEP4 plasmids. Alt FP/pcDNA3.1 plasmids were used for transient transfection, and Alt FP/pCEP4 plasmids were used for stable transfection. Full length $Ga_{16}$ cDNA was subcloned into the pcDNA3.1 vector. The plasmids were sequenced by Sequetech.

HEK 293/EBNA cells were obtained from the American Type Culture Collection (ATCC). HEK 293/EBNA cells were routinely maintained in DMEM with 10% fetal bovine serum, 1% glutamine, 0.5% penicillin/streptomycin. Cells were kept in humidified 5% $CO_2$, 95% air at 37° C. For stable transfection, Alt FP/pCEP4 plasmids were transfected into HEK 293/EBNA cells using Fugene 6 (Roche Diagnostics Corp., Inc.; Indianapolis, Ind.), according to the manufacture's instructions, and then 200 mg/ml hygromycin was used to select cell clones that stably expressed the plasmid.

EXAMPLE II

Tissue Distribution of Alternatively Spliced FP Receptor Variants

This example shows the tissue distribution of alternatively spliced FP receptor variant VAR-1 to VAR-6 mRNA using RT-PCR.

Human multiple tissue RNA samples were purchased from BD Biosciences (Clontech). Using 5 µg of human total RNA, first strand cDNA was synthesized by Superscript II Rnase H reverse transcriptase (Life Technologies). Reactions (20 µl) containing 5 µl of RNA, 250 ng of oligo (dT), and 100 units of reverse transcriptase were incubated at 42° C. for 1 hour and terminated by 100° C. for 3 minutes.

PCR reactions contained the following: PCR buffer (10 mM Tris-HCl, pH 8.3, 50 mM KCl, 2 mM MgCl), 2.5 units AmpliTaq DNA polymerase, 0.2 µM forward and reverse primers, in a final volume of 50 µl. After an initial incubation for 5 minutes at 94° C., samples were subjected to 30 cycles of 30 seconds at 95° C., 30 seconds at 58° C., and 30 seconds at 72° C. in a PE 9700 thermal cycler.

Multiple tissue RT-PCR analysis was performed to detect alternatively spliced FP receptor variant mRNA using the following primers:

```
VAR-1 and VAR-2
forward: TGCAATGCAATCACAGGAAT    (SEQ ID NO: 15)

reverse: CACTCCACAGCATTGACTGG    (SEQ ID NO: 16)

VAR-2 and VAR-3
forward: GAGCCCATTTCTGGGATACA    (SEQ ID NO: 35)

reverse: AGTGCCTCTCTTCACCCTCA    (SEQ ID NO: 36)

VAR-4
forward: AGCCCATTTCTGCGATAAGA    (SEQ ID NO: 37)

reverse: GTTCTGGAGCCTCAGGTGTC    (SEQ ID NO: 38)

VAR-5 and VAR-6
forward: AGCTCCTGGCGATAATGTGT    (SEQ ID NO: 39)

reverse: CCYYCHCAAYAHYCCYCCAA    (SEQ ID NO: 40)
```

EXAMPLE III

Screening Assays using Alternatively Spliced FP Receptor Variants

This example describes a FLIPR and luciferase assay for screening compounds against alternatively spliced FP receptor variants.

HEK 293/EBNA cells transiently or stably expressing Alt FP/pcDNA3.1 plasmids were seeded at a density of $5 \times 10^3$ cells per well in Biocoat® Poly-D-lysine-coated black-wall, clear-bottom 96-well plates (Becton-Dickinson; Franklin Lakes, N.J.) and allowed to attach overnight. At 48 hours after transfection, the cells were washed two times with HBSS-HEPES buffer (Hanks Balanced Salt Solution without bicarbonate and phenol red, 20 mM HEPES, pH 7.4) using a Lab Systems Cellwash plate washer. After 45 minutes of dye-loading in the dark, using the calcium-sensitive dye Fluo-4 AM at a final concentration of 2 mM, the plates were washed four times with HBSS-HEPES buffer to remove excess dye leaving 100 ml in each well. Plates were re-equilibrated to 37° C. for a few minutes. The cells were excited with an Argon laser at 488 nm, and emission was measured through a 510-570 nm bandwidth emission filter (FLIPR™; Molecular Devices; Sunnyvale, Calif.). Compound solution was added in a 50 ml volume to each well to give the desired final concentration. The peak increase in fluorescence intensity was recorded for each well. To generate concentration-response curves, compounds were tested in duplicate in a concentration range between $10^{-11}$ and $10^{-5}$ M. The duplicate values were averaged.

CRE-luciferase reporter plasmids purchased from Invitrogen were used for detecting cAMP accumulation in $G_{as}$ coupled receptors. pGL3-N-960 plasmids containing human Nur77 promoter (Uemura et al., *J. Biol. Chem.* 270:5427-5433 (1995)) and pGL3-CTGF-LUC plasmids containing human CTGF promoter were used for detecting calcium, PKC, and MAP kinase pathways associated with $G_{aq}$ coupled receptors. For the pGL3-CTGF-LUC plasmid, a DNA fragment containing the CTGF promoter region from −2047 to +65 (Fu et al., *J. Biol. Chem* 276:45888-45894 (2001)) was cloned from human genomic DNA (Clontech). The fragment was subcloned into a pGL3 luciferase expression vector (Promega Inc.) creating the pGL3-CTGF-LUC plasmid.

Luciferase reporter plasmids were transfected into HEK 293/EBNA cells transiently or stably expressing alternatively spliced FP receptor variants using Fugene 6, according to the manufacturer's instructions. In brief, the cells were plated in 24 well plates overnight, and then the 24 well plate cells were washed twice and resuspended in 1 ml of DMEM. The cell suspension was mixed with 0.2 μg of plasmid DNA in 100 μl of DMEM containing 0.6 μl Fugene 6 solution and added into each well. Plates were cultured for 24 hours at 37° C. before compounds were added to the cultures at concentrations ranging from $10^{-11}$ to $10^{-6}$ M. Cells were harvested 6 hours later and lysed in 100 μl of 25 mM Tris-phosphate buffer (pH 7.5) containing 1% Triton X-100. Soluble extracts (20 μl) were assayed for luciferase activity as described below.

The luciferase assay was performed with a Promega assay kit (Promega, Inc.; Madison, Wis.) at room temperature using an Autolumat LB 953 (Berthold; Bad Wildbad, Germany). Luciferase content was measured by calculating the light emitted during the initial 10 seconds of the reaction. Relative luciferase activity was expressed as fold values of ratio compared to control. Experiments were independently repeated at least 3 times.

All journal article, reference and patent citations provided herein, including referenced sequence accession numbers of nucleotide and amino acid sequences contained in various databases, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. An isolated polypeptide, comprising the amino acid sequence of SEQ ID NO:24.

2. An isolated polypeptide, comprising the amino acid sequence of SEQ ID NO:8.

3. A method for identifying a compound that modulates a FP receptor variant, comprising: a) contacting said FP receptor variant with a compound, wherein said FP receptor variant is an isolated FP receptor variant or a FP receptor variant over-expressed in a genetically engineered cell, and b) determining the level of an indicator, which correlates with modulation of a FP receptor variant, wherein an alteration in the level of said indicator as compared to a control level indicates that said compound is a compound that modulates a FP receptor variant, wherein said FP receptor variant in step (a) is a polypeptide comprising the amino acid sequence of SEQ ID NO:24.

4. A method for identifying a compound that modulates a FP receptor variant, comprising: a) contacting said FP receptor variant with a compound, wherein said FP receptor variant is an isolated FP receptor variant or a FP receptor variant over-expressed in a genetically engineered cell, and b) determining the level of an indicator, which correlates with modulation of a FP receptor variant, wherein an alteration in the level of said indicator as compared to a control level indicates that said compound is a compound that modulates a FP receptor variant, wherein said EP receptor variant in step (a) is a polypeptide comprising the amino acid sequence of SEQ ID NO:8.

5. A method for identifying a compound that specifically binds to a FP receptor variant, comprising: a) contacting said FP receptor variant with a compound, wherein said FP receptor variant is an isolated FP receptor variant or a FP receptor variant over-expressed in a genetically engineered cell, and b) determining specific binding of said compound to said FP receptor variant, wherein said FP receptor variant in step (a) a polypeptide compromising the amino acid sequence of SEQ ID NO:24.

6. A method for identifying a compound that specifically binds to a FP receptor variant, comprising: a) contacting said FP receptor variant with a compound, wherein said FP receptor variant is an isolated FP receptor variant or a FP receptor variant over-expressed in a genetically engineered cell, and b) determining specific binding of said compound to said FP receptor variant, wherein said FP receptor variant in step (a) is a polypeptide comprising the amino acid sequence of SEQ ID NO:8.

7. A method for identifying a compound that differentially modulates a FP receptor variant, comprising: a) contacting said FP receptor variant with a compound, wherein said FP receptor variant is an isolated FP receptor variant or a FP receptor variant over-expressed in a genetically engineered cell; b) determining the level of an indicator which correlates with modulation of said FP receptor variant; c) contacting a second receptor with said compound; d) determining the level of a corresponding indicator which correlates with modulation of said second receptor; and e) comparing the level of the indicator from step (b) with the level of the corresponding indicator from step (d), wherein a different level of the indicator from step (b) compared to the level of the corresponding indicator from step (d) indicates that said compound is a compound that differentially modulates said FP receptor variant, wherein said FP receptor variant in step (a) is a polypeptide comprising the amino acid sequence of SEQ ID NO:24.

8. A method for identifying a compound that differentially modulates a FP receptor variant, comprising: a) contacting said EP receptor variant with a compound, wherein said FP receptor variant is an isolated FP receptor variant or a FP receptor variant over-expressed in a genetically engineered cell; b) determining the level of an indicator which correlates with modulation of said FP receptor variant; c) contacting a second receptor with said compound; d) determining the level of a corresponding indicator which correlates with modulation of said second receptor; and e) comparing the level of the indicator from step (b) with the level of the corresponding indicator from step (d), wherein a different level of the indicator from step (b) compared to the level of the corresponding indicator from step (d) indicates that said compound is a compound that differentially modulates said FP receptor variant, wherein said FP receptor variant in step (a) is a polypeptide comprising the amino acid sequence of SEQ ID NO:8.

9. A method for identifying a compound that differentially binds to a FP receptor variant, comprising: a) contacting said FP receptor variant with a compound, wherein said FP receptor variant is an isolated FP receptor or a FP receptor variant over-expressed in a genetically engineered cell; b) determining specific binding of said compound to said FP receptor variant; c) contacting a second receptor with said compound; d) determining specific binding of said compound to said second receptor; and e) comparing the level of specific binding from step (b) with the level of specific binding from step (d), wherein a different level of specific binding from step (b) compared to the level of specific binding from step (d) indicates that said compound is a compound that differentially binds to a FP receptor variant, wherein said FP receptor variant in step (a) is a polypeptide comprising the amino acid sequence of SEQ ID NO:24.

10. A method for identifying a compound that differentially binds to a FP receptor variant, comprising: a) contacting said FP receptor variant with a compound, wherein said FP receptor variant is an isolated FP receptor or a FP receptor variant over-expressed in a genetically engineered cell; b) determining specific binding of said compound to said FP receptor variant; c) contacting a second receptor with said compound; d) determining specific binding of said compound to said second receptor; and e) comparing the level of specific binding from step (b) with the level of specific binding from step (d), wherein a different level of specific binding from step (b) compared to the level of specific binding from step (d) indicates that said compound is a compound that differentially binds to a FP receptor variant, wherein said FP receptor variant in step (a) is a polypeptide comprising the amino acid sequence of SEQ ID NO:8.

* * * * *

UNITED STATES PATENT AND TRADEMARK OFFICE
CERTIFICATE OF CORRECTION

PATENT NO. : 7,320,871 B2
APPLICATION NO. : 10/620289
DATED : January 22, 2008
INVENTOR(S) : Liang et al.

It is certified that error appears in the above-identified patent and that said Letters Patent is hereby corrected as shown below:

Title Page;
On Page 2, in field (56), under "Other Publications", in column 1, line 10, delete "of" and insert -- on --, therefor.

In column 7, line 46, delete "al," and insert -- al., --, therefor.

In column 7, line 50, delete "these" and insert -- these, --, therefor.

In column 7, line 61, delete "26." and insert -- 26: --, therefor.

In column 7, line 64, delete "protaglandins" and insert -- prostaglandins --, therefor.

In column 7, line 67, delete "Reorod." and insert -- Reprod. --, therefor.

In column 8, line 1, delete "Exo." and insert -- Exp. --, therefor.

In column 13, line 9, delete "11," and insert -- 18, --, therefor.

In column 13, line 43, delete "25" and insert -- 25, --, therefor.

In column 13, line 46, delete "$M^1$" and insert -- $M^{-1}$ --, therefor.

In column 14, line 34, delete "Engineerinq," and insert -- Engineering, --, therefor.

In column 15, line 48, delete "mammory" and insert -- mammary --, therefor.

In column 21, line 15, delete "limiation," and insert -- limitation, --, therefor.

In column 30, line 39, delete "bioavailablility" and insert -- bioavailability --, therefor.

In column 33, line 60, delete "sapeins" and insert -- sapiens --, therefor.

In column 37, line 8, delete "sapeins" and insert -- sapiens --, therefor.

In column 73, line 27, in Claim 4, delete "EP" and insert -- FP --, therefor.

In column 73, line 37, in Claim 5, delete "compromising" and insert -- comprising --, therfor.

UNITED STATES PATENT AND TRADEMARK OFFICE
CERTIFICATE OF CORRECTION

PATENT NO. : 7,320,871 B2
APPLICATION NO. : 10/620289
DATED : January 22, 2008
INVENTOR(S) : Liang et al.

It is certified that error appears in the above-identified patent and that said Letters Patent is hereby corrected as shown below:

In column 73, line 46, in Claim 6, delete "compromising" and insert -- comprising --, therefor.

In column 74, line 9, in Claim 8, delete "EP" and insert -- FP --, therefor.

Signed and Sealed this

Thirteenth Day of May, 2008

JON W. DUDAS
*Director of the United States Patent and Trademark Office*

SEQUENCE LISTING

```
<160> NUMBER OF SEQ ID NOS: 40

<210> SEQ ID NO 1
<211> LENGTH: 1151
<212> TYPE: DNA
<213> ORGANISM: Homo sapeins
<220> FEATURE:
```

```
<221> NAME/KEY: CDS
<222> LOCATION: (1)...(894)

<400> SEQUENCE: 1
```

| | | | | | | | | | | | | | | | | |
|---|---|---|---|---|---|---|---|---|---|---|---|---|---|---|---|---|
| atg | tcc | atg | aac | aat | tcc | aaa | cag | cta | gtg | tct | cct | gca | gct | gcg | ctt | 48 |
| Met | Ser | Met | Asn | Asn | Ser | Lys | Gln | Leu | Val | Ser | Pro | Ala | Ala | Ala | Leu | |
| 1 | | | | 5 | | | | | 10 | | | | | 15 | | |
| ctt | tca | aac | aca | acc | tgc | cag | acg | gaa | aac | cgg | ctt | tcc | gta | ttt | ttt | 96 |
| Leu | Ser | Asn | Thr | Thr | Cys | Gln | Thr | Glu | Asn | Arg | Leu | Ser | Val | Phe | Phe | |
| | | | 20 | | | | | 25 | | | | | 30 | | | |
| tca | gta | atc | ttc | atg | aca | gtg | gga | atc | ttg | tca | aac | agc | ctt | gcc | atc | 144 |
| Ser | Val | Ile | Phe | Met | Thr | Val | Gly | Ile | Leu | Ser | Asn | Ser | Leu | Ala | Ile | |
| | | 35 | | | | | 40 | | | | | 45 | | | | |
| gcc | att | ctc | atg | aag | gca | tat | cag | aga | ttt | aga | cag | aag | tcc | aag | gca | 192 |
| Ala | Ile | Leu | Met | Lys | Ala | Tyr | Gln | Arg | Phe | Arg | Gln | Lys | Ser | Lys | Ala | |
| | 50 | | | | | 55 | | | | | 60 | | | | | |
| tcg | ttt | ctg | ctt | ttg | gcc | agc | ggc | ctg | gta | atc | act | gat | ttc | ttt | ggc | 240 |
| Ser | Phe | Leu | Leu | Leu | Ala | Ser | Gly | Leu | Val | Ile | Thr | Asp | Phe | Phe | Gly | |
| 65 | | | | | 70 | | | | | 75 | | | | | 80 | |
| cat | ctc | atc | aat | gga | gcc | ata | gca | gta | ttt | gta | tat | gct | tct | gat | aaa | 288 |
| His | Leu | Ile | Asn | Gly | Ala | Ile | Ala | Val | Phe | Val | Tyr | Ala | Ser | Asp | Lys | |
| | | | | 85 | | | | | 90 | | | | | 95 | | |
| gaa | tgg | atc | cgc | ttt | gac | caa | tca | aat | gtc | ctt | tgc | agt | att | ttt | ggt | 336 |
| Glu | Trp | Ile | Arg | Phe | Asp | Gln | Ser | Asn | Val | Leu | Cys | Ser | Ile | Phe | Gly | |
| | | | 100 | | | | | 105 | | | | | 110 | | | |
| atc | tgc | atg | gtg | ttt | tct | ggt | ctg | tgc | cca | ctt | ctt | cta | ggc | agt | gtg | 384 |
| Ile | Cys | Met | Val | Phe | Ser | Gly | Leu | Cys | Pro | Leu | Leu | Leu | Gly | Ser | Val | |
| | | 115 | | | | | 120 | | | | | 125 | | | | |
| atg | gcc | att | gag | cgg | tgt | att | gga | gtc | aca | aaa | cca | ata | ttt | cat | tct | 432 |
| Met | Ala | Ile | Glu | Arg | Cys | Ile | Gly | Val | Thr | Lys | Pro | Ile | Phe | His | Ser | |
| | 130 | | | | | 135 | | | | | 140 | | | | | |
| acg | aaa | att | aca | tcc | aaa | cat | gtg | aaa | atg | atg | tta | agt | ggt | gtg | tgc | 480 |
| Thr | Lys | Ile | Thr | Ser | Lys | His | Val | Lys | Met | Met | Leu | Ser | Gly | Val | Cys | |
| 145 | | | | | 150 | | | | | 155 | | | | | 160 | |
| ttg | ttt | gct | gtt | ttc | ata | gct | ttg | ctg | ccc | atc | ctt | gga | cat | cga | gac | 528 |
| Leu | Phe | Ala | Val | Phe | Ile | Ala | Leu | Leu | Pro | Ile | Leu | Gly | His | Arg | Asp | |
| | | | | 165 | | | | | 170 | | | | | 175 | | |
| tat | aaa | att | cag | gcg | tcg | agg | acc | tgg | tgt | ttc | tac | aac | aca | gaa | gac | 576 |
| Tyr | Lys | Ile | Gln | Ala | Ser | Arg | Thr | Trp | Cys | Phe | Tyr | Asn | Thr | Glu | Asp | |
| | | | 180 | | | | | 185 | | | | | 190 | | | |
| atc | aaa | gac | tgg | gaa | gat | aga | ttt | tat | ctt | cta | ctt | ttt | tct | ttt | ctg | 624 |
| Ile | Lys | Asp | Trp | Glu | Asp | Arg | Phe | Tyr | Leu | Leu | Leu | Phe | Ser | Phe | Leu | |
| | | 195 | | | | | 200 | | | | | 205 | | | | |
| ggg | ctc | tta | gcc | ctt | ggt | gtt | tca | ttg | ttg | tgc | aat | gca | atc | aca | gga | 672 |
| Gly | Leu | Leu | Ala | Leu | Gly | Val | Ser | Leu | Leu | Cys | Asn | Ala | Ile | Thr | Gly | |
| | 210 | | | | | 215 | | | | | 220 | | | | | |
| att | aca | ctt | tta | aga | gtt | aaa | ttt | aaa | agt | cag | cag | cac | aga | caa | ggc | 720 |
| Ile | Thr | Leu | Leu | Arg | Val | Lys | Phe | Lys | Ser | Gln | Gln | His | Arg | Gln | Gly | |
| 225 | | | | | 230 | | | | | 235 | | | | | 240 | |
| aga | tct | cat | cat | ttg | gaa | atg | gta | atc | cag | ctc | ctg | gcg | ata | atg | tgt | 768 |
| Arg | Ser | His | His | Leu | Glu | Met | Val | Ile | Gln | Leu | Leu | Ala | Ile | Met | Cys | |
| | | | | 245 | | | | | 250 | | | | | 255 | | |
| gtc | tcc | tgt | att | tgt | tgg | agc | cca | ttt | ctg | gga | tac | aga | ata | att | ttg | 816 |
| Val | Ser | Cys | Ile | Cys | Trp | Ser | Pro | Phe | Leu | Gly | Tyr | Arg | Ile | Ile | Leu | |
| | | | 260 | | | | | 265 | | | | | 270 | | | |
| aat | ggg | aaa | gag | aaa | tat | aaa | gta | tat | gaa | gag | caa | agt | gat | ttc | tta | 864 |
| Asn | Gly | Lys | Glu | Lys | Tyr | Lys | Val | Tyr | Glu | Glu | Gln | Ser | Asp | Phe | Leu | |
| | | 275 | | | | | 280 | | | | | 285 | | | | |
| cat | agg | tta | caa | tgg | cca | aca | ttg | gaa | taa | atggaaatca | ttctctggaa | | | | | 914 |
| His | Arg | Leu | Gln | Trp | Pro | Thr | Leu | Glu | * | | | | | | | |

```
                    290                 295
acctgtgaaa caacactttt tgctctccga atggcaacat ggaatcaaat cttagatcct    974
tgggtatata ttcttctacg aaaggctgtc cttaagaatc tctataagct tgccagtcaa   1034
tgctgtggag tgcatgtcat cagcttacat atttgggagc ttagttccat taaaaattcc   1094
ttaaaggttg ctgctatttc tgagtcacca gttgcagaga aatcagcaag cacctag      1151
```

<210> SEQ ID NO 2
<211> LENGTH: 297
<212> TYPE: PRT
<213> ORGANISM: Homo sapeins

<400> SEQUENCE: 2

```
Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
             20                  25                  30

Ser Val Ile Phe Met Thr Val Gly Ile Leu Ser Asn Ser Leu Ala Ile
         35                  40                  45

Ala Ile Leu Met Lys Ala Tyr Gln Arg Phe Arg Gln Lys Ser Lys Ala
     50                  55                  60

Ser Phe Leu Leu Leu Ala Ser Gly Leu Val Ile Thr Asp Phe Phe Gly
 65                  70                  75                  80

His Leu Ile Asn Gly Ala Ile Ala Val Phe Val Tyr Ala Ser Asp Lys
                 85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Gly Tyr Arg Ile Ile Leu
            260                 265                 270

Asn Gly Lys Glu Lys Tyr Lys Val Tyr Glu Glu Gln Ser Asp Phe Leu
        275                 280                 285

His Arg Leu Gln Trp Pro Thr Leu Glu
    290                 295
```

<210> SEQ ID NO 3
<211> LENGTH: 1222
<212> TYPE: DNA

<213> ORGANISM: Homo sapiens
<220> FEATURE:
<221> NAME/KEY: CDS
<222> LOCATION: (1)...(828)

<400> SEQUENCE: 3

```
atg tcc atg aac aat tcc aaa cag cta gtg tct cct gca gct gcg ctt        48
Met Ser Met Asn Asn Ser Lys Gln Leu Val Ser Pro Ala Ala Ala Leu
 1               5                  10                  15 ctt tca aac aca acc tgc cag acg gaa aac cgg ctt tcc gta ttt ttt        96
Leu Ser Asn Thr Thr Cys Gln Thr Glu Asn Arg Leu Ser Val Phe Phe
             20                  25                  30 tca gta atc ttc atg aca gtg gga atc ttg tca aac agc ctt gcc atc       144
Ser Val Ile Phe Met Thr Val Gly Ile Leu Ser Asn Ser Leu Ala Ile
         35                  40                  45 gcc att ctc atg aag gca tat cag aga ttt aga cag aag tcc aag gca       192
Ala Ile Leu Met Lys Ala Tyr Gln Arg Phe Arg Gln Lys Ser Lys Ala
     50                  55                  60 tcg ttt ctg ctt ttg gcc agc ggc ctg gta atc act gat ttc ttt ggc       240
Ser Phe Leu Leu Leu Ala Ser Gly Leu Val Ile Thr Asp Phe Phe Gly
 65                  70                  75                  80 cat ctc atc aat gga gcc ata gca gta ttt gta tat gct tct gat aaa       288
His Leu Ile Asn Gly Ala Ile Ala Val Phe Val Tyr Ala Ser Asp Lys
                 85                  90                  95 gaa tgg atc cgc ttt gac caa tca aat gtc ctt tgc agt att ttt ggt       336
Glu Trp Ile Arg Phe Asp Gln Ser Asn Val Leu Cys Ser Ile Phe Gly
            100                 105                 110 atc tgc atg gtg ttt tct ggt ctg tgc cca ctt ctt cta ggc agt gtg       384
Ile Cys Met Val Phe Ser Gly Leu Cys Pro Leu Leu Leu Gly Ser Val
        115                 120                 125 atg gcc att gag cgg tgt att gga gtc aca aaa cca ata ttt cat tct       432
Met Ala Ile Glu Arg Cys Ile Gly Val Thr Lys Pro Ile Phe His Ser
    130                 135                 140 acg aaa att aca tcc aaa cat gtg aaa atg atg tta agt ggt gtg tgc       480
Thr Lys Ile Thr Ser Lys His Val Lys Met Met Leu Ser Gly Val Cys
145                 150                 155                 160 ttg ttt gct gtt ttc ata gct ttg ctc ccc atc ctt gga cat cga gac       528
Leu Phe Ala Val Phe Ile Ala Leu Leu Pro Ile Leu Gly His Arg Asp
                165                 170                 175 tat aaa att cag gcg tcg agg acc tgg tgt ttc tac aac aca gaa gac       576
Tyr Lys Ile Gln Ala Ser Arg Thr Trp Cys Phe Tyr Asn Thr Glu Asp
            180                 185                 190 atc aaa gac tgg gaa gat aga ttt tat ctt cta ctt ttt tct ttt ctg       624
Ile Lys Asp Trp Glu Asp Arg Phe Tyr Leu Leu Leu Phe Ser Phe Leu
        195                 200                 205 ggg ctc tta gcc ctt ggt gtt tca ttg ttg tgc aat gca atc aca gga       672
Gly Leu Leu Ala Leu Gly Val Ser Leu Leu Cys Asn Ala Ile Thr Gly
    210                 215                 220 att aca ctt tta aga gtt aaa ttt aaa agt cag cag cac aga caa ggc       720
Ile Thr Leu Leu Arg Val Lys Phe Lys Ser Gln Gln His Arg Gln Gly
225                 230                 235                 240 aga tct cat cat ttg gaa atg gta atc cag ctc ctg gcg ata atg tgt       768
Arg Ser His His Leu Glu Met Val Ile Gln Leu Leu Ala Ile Met Cys
                245                 250                 255 gtc tcc tgt att tgt tgg agc cca ttt ctg aaa ata gaa gga aaa ata       816
Val Ser Cys Ile Cys Trp Ser Pro Phe Leu Lys Ile Glu Gly Lys Ile
            260                 265                 270 aaa gtc aca tga gtgaaggaga aacagaacgc aagggtgaaa acaaggcaat           868
Lys Val Thr *
        275
```

```
tagggcagca gaaagctggt ggtatgaggg tgaagagagg cactctcatg ttttgggaac      928
tctgttggaa aggttacaat ggccaacatt ggaataaatg gaaatcattc tctggaaacc      988
tgtgaaacaa cacttttgc tctccgaatg gcaacatgga atcaaatctt agatccttgg     1048
gtatatattc ttctacgaaa ggctgtcctt aagaatctct ataagcttgc cagtcaatgc     1108
tgtggagtgc atgtcatcag cttacatatt tgggagctta gttccattaa aaattcctta     1168
aaggttgctg ctatttctga gtcaccagtt gcagagaaat cagcaagcac ctag           1222
```

<210> SEQ ID NO 4
<211> LENGTH: 275
<212> TYPE: PRT
<213> ORGANISM: Homo sapiens

<400> SEQUENCE: 4

```
Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
    50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Lys Ile Glu Gly Lys Ile
            260                 265                 270

Lys Val Thr
        275
```

<210> SEQ ID NO 5
<211> LENGTH: 1293
<212> TYPE: DNA
<213> ORGANISM: Homo sapiens

```
<220> FEATURE:
<221> NAME/KEY: CDS
<222> LOCATION: (1)...(876)

<400> SEQUENCE: 5 atg tcc atg aac aat tcc aaa cag cta gtg tct cct gca gct gcg ctt        48
Met Ser Met Asn Asn Ser Lys Gln Leu Val Ser Pro Ala Ala Ala Leu
 1               5                  10                  15 ctt tca aac aca acc tgc cag acg gaa aac cgg ctt tcc gta ttt ttt        96
Leu Ser Asn Thr Thr Cys Gln Thr Glu Asn Arg Leu Ser Val Phe Phe
             20                  25                  30 tca gta atc ttc atg aca gtg gga atc ttg tca aac agc ctt gcc atc       144
Ser Val Ile Phe Met Thr Val Gly Ile Leu Ser Asn Ser Leu Ala Ile
         35                  40                  45 gcc att ctc atg aag gca tat cag aga ttt aga cag aag tcc aag gca       192
Ala Ile Leu Met Lys Ala Tyr Gln Arg Phe Arg Gln Lys Ser Lys Ala
     50                  55                  60 tcg ttt ctg ctt ttg gcc agc ggc ctg gta atc act gat ttc ttt ggc       240
Ser Phe Leu Leu Leu Ala Ser Gly Leu Val Ile Thr Asp Phe Phe Gly
 65                  70                  75                  80 cat ctc atc aat gga gcc ata gca gta ttt gta tat gct tct gat aaa       288
His Leu Ile Asn Gly Ala Ile Ala Val Phe Val Tyr Ala Ser Asp Lys
                 85                  90                  95 gaa tgg atc cgc ttt gac caa tca aat gtc ctt tgc agt att ttt ggt       336
Glu Trp Ile Arg Phe Asp Gln Ser Asn Val Leu Cys Ser Ile Phe Gly
            100                 105                 110 atc tgc atg gtg ttt tct ggt ctg tgc cca ctt ctt cta ggc agt gtg       384
Ile Cys Met Val Phe Ser Gly Leu Cys Pro Leu Leu Leu Gly Ser Val
        115                 120                 125 atg gcc att gag cgg tgt att gga gtc aca aaa cca ata ttt cat tct       432
Met Ala Ile Glu Arg Cys Ile Gly Val Thr Lys Pro Ile Phe His Ser
    130                 135                 140 acg aaa att aca tcc aaa cat gtg aaa atg atg tta agt ggt gtg tgc       480
Thr Lys Ile Thr Ser Lys His Val Lys Met Met Leu Ser Gly Val Cys
145                 150                 155                 160 ttg ttt gct gtt ttc ata gct ttg ctg ccc atc ctt gga cat cga gac       528
Leu Phe Ala Val Phe Ile Ala Leu Leu Pro Ile Leu Gly His Arg Asp
                165                 170                 175 tat aaa att cag gcg tcg agg acc tgg tgt ttc tac aac aca gaa gac       576
Tyr Lys Ile Gln Ala Ser Arg Thr Trp Cys Phe Tyr Asn Thr Glu Asp
            180                 185                 190 atc aaa gac tgg gaa gat aga ttt tat ctt cta ctt ttt tct ttt ctg       624
Ile Lys Asp Trp Glu Asp Arg Phe Tyr Leu Leu Leu Phe Ser Phe Leu
        195                 200                 205 ggg ctc tta gcc ctt ggt gtt tca ttg ttg tgc aat gca atc aca gga       672
Gly Leu Leu Ala Leu Gly Val Ser Leu Leu Cys Asn Ala Ile Thr Gly
    210                 215                 220 att aca ctt tta aga gtt aaa ttt aaa agt cag cag cac aga caa ggc       720
Ile Thr Leu Leu Arg Val Lys Phe Lys Ser Gln Gln His Arg Gln Gly
225                 230                 235                 240 aga tct cat cat ttg gaa atg gta atc cag ctc ctg gcg ata atg tgt       768
Arg Ser His His Leu Glu Met Val Ile Gln Leu Leu Ala Ile Met Cys
                245                 250                 255 gtc tcc tgt att tgt tgg agc cca ttt ctg gga tac aga ata att ttg       816
Val Ser Cys Ile Cys Trp Ser Pro Phe Leu Gly Tyr Arg Ile Ile Leu
            260                 265                 270 aat ggg aaa gag aaa tat aaa gta tat gaa gag caa agt gat ttc tta       864
Asn Gly Lys Glu Lys Tyr Lys Val Tyr Glu Glu Gln Ser Asp Phe Leu
        275                 280                 285 cat aga aaa tag aaggaaaaat aaaagtcaca tgagtgaagg agaaacagaa           916
His Arg Lys
```

```
His Arg Lys  *
    290 cgcaaggtg   aaaacaaggc  aattagggca  gcagaaagct  ggtggtatga  gggtgaagag    976
aggcactctc  atgttttggg  aactctgttg  gaaaggttac  aatggccaac  attggaataa   1036
atggaaatca  ttctctggaa  acctgtgaaa  caacactttt  tgctctccga  atggcaacat   1096
ggaatcaaat  cttagatcct  tgggtatata  ttcttctacg  aaaggctgtc  cttaagaatc   1156
tctataagct  tgccagtcaa  tgctgtggag  tgcatgtcat  cagcttacat  atttgggagc   1216
ttagttccat  taaaaattcc  ttaaaggttg  ctgctatttc  tgagtcacca  gttgcagaga   1276
aatcagcaag  caccctag                                                    1293

<210> SEQ ID NO 6
<211> LENGTH: 291
<212> TYPE: PRT
<213> ORGANISM: Homo sapiens

<400> SEQUENCE: 6

Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
                20                  25                  30

Ser Val Ile Phe Met Thr Val Gly Ile Leu Ser Asn Ser Leu Ala Ile
                35                  40                  45

Ala Ile Leu Met Lys Ala Tyr Gln Arg Phe Arg Gln Lys Ser Lys Ala
            50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Gly Tyr Arg Ile Ile Leu
            260                 265                 270

Asn Gly Lys Glu Lys Tyr Lys Val Tyr Glu Glu Gln Ser Asp Phe Leu
        275                 280                 285
```

His Arg Lys
    290

<210> SEQ ID NO 7
<211> LENGTH: 1176
<212> TYPE: DNA
<213> ORGANISM: Homo sapiens
<220> FEATURE:
<221> NAME/KEY: CDS
<222> LOCATION: (1)...(891)

<400> SEQUENCE: 7

```
atg tcc atg aac aat tcc aaa cag cta gtg tct cct gca gct gcg ctt      48
Met Ser Met Asn Asn Ser Lys Gln Leu Val Ser Pro Ala Ala Ala Leu
 1               5                  10                  15 ctt tca aac aca acc tgc cag acg gaa aac cgg ctt tcc gta ttt ttt      96
Leu Ser Asn Thr Thr Cys Gln Thr Glu Asn Arg Leu Ser Val Phe Phe
             20                  25                  30 tca gta atc ttc atg aca gtg gga atc ttg tca aac agc ctt gcc atc     144
Ser Val Ile Phe Met Thr Val Gly Ile Leu Ser Asn Ser Leu Ala Ile
         35                  40                  45 gcc att ctc atg aag gca tat cag aga ttt aga cag aag tcc aag gca     192
Ala Ile Leu Met Lys Ala Tyr Gln Arg Phe Arg Gln Lys Ser Lys Ala
     50                  55                  60 tcg ttt ctg ctt ttg gcc agc ggc ctg gta atc act gat ttc ttt ggc     240
Ser Phe Leu Leu Leu Ala Ser Gly Leu Val Ile Thr Asp Phe Phe Gly
 65                  70                  75                  80 cat ctc atc aat gga gcc ata gca gta ttt gta tat gct tct gat aaa     288
His Leu Ile Asn Gly Ala Ile Ala Val Phe Val Tyr Ala Ser Asp Lys
                 85                  90                  95 gaa tgg atc cgc ttt gac caa tca aat gtc ctt tgc agt att ttt ggt     336
Glu Trp Ile Arg Phe Asp Gln Ser Asn Val Leu Cys Ser Ile Phe Gly
            100                 105                 110 atc tgc atg gtg ttt tct ggt ctg tgc cca ctt ctt cta ggc agt gtg     384
Ile Cys Met Val Phe Ser Gly Leu Cys Pro Leu Leu Leu Gly Ser Val
        115                 120                 125 atg gcc att gag cgg tgt att gga gtc aca aaa cca ata ttt cat tct     432
Met Ala Ile Glu Arg Cys Ile Gly Val Thr Lys Pro Ile Phe His Ser
    130                 135                 140 acg aaa att aca tcc aaa cat gtg aaa atg atg tta agt ggt gtg tgc     480
Thr Lys Ile Thr Ser Lys His Val Lys Met Met Leu Ser Gly Val Cys
145                 150                 155                 160 ttg ttt gct gtt ttc ata gct ttg ctg ccc atc ctt gga cat cga gac     528
Leu Phe Ala Val Phe Ile Ala Leu Leu Pro Ile Leu Gly His Arg Asp
                165                 170                 175 tat aaa att cag gcg tcg agg acc tgg tgt ttc tac aac aca gaa gac     576
Tyr Lys Ile Gln Ala Ser Arg Thr Trp Cys Phe Tyr Asn Thr Glu Asp
            180                 185                 190 atc aaa gac tgg gaa gat aga ttt tat ctt cta ctt ttt tct ttt ctg     624
Ile Lys Asp Trp Glu Asp Arg Phe Tyr Leu Leu Leu Phe Ser Phe Leu
        195                 200                 205 ggg ctc tta gcc ctt ggt gtt tca ttg ttg tgc aat gca atc aca gga     672
Gly Leu Leu Ala Leu Gly Val Ser Leu Leu Cys Asn Ala Ile Thr Gly
    210                 215                 220 att aca ctt tta aga gtt aaa ttt aaa agt cag cag cac aga caa ggc     720
Ile Thr Leu Leu Arg Val Lys Phe Lys Ser Gln Gln His Arg Gln Gly
225                 230                 235                 240 aga tct cat cat ttg gaa atg gta atc cag ctc ctg gcg ata atg tgt     768
Arg Ser His His Leu Glu Met Val Ile Gln Leu Leu Ala Ile Met Cys
                245                 250                 255 gtc tcc tgt att tgt tgg agc cca ttt ctg gtg aaa gaa act cat ctc     816
```

```
                Val Ser Cys Ile Cys Trp Ser Pro Phe Leu Val Lys Glu Thr His Leu
                            260                 265                 270 cag atg aga ctt tgg act tgg gac ttt cga gtt aat gct ttg gag gac          864
Gln Met Arg Leu Trp Thr Trp Asp Phe Arg Val Asn Ala Leu Glu Asp
        275                 280                 285 tat tgc gaa ggc ttg act gta ttt tga aatgttacaa tggccaacat                911
Tyr Cys Glu Gly Leu Thr Val Phe  *
        290                 295 tggaataaat ggaaatcatt ctctggaaac ctgtgaaaca acacttttg ctctccgaat          971 ggcaacatgg aatcaaatct tagatccttg ggtatatatt cttctacgaa aggctgtcct       1031
taagaatctc tataagcttg ccagtcaatg ctgtggagtg catgtcatca gcttacatat       1091
ttgggagctt agttccatta aaaattcctt aaaggttgct gctatttctg agtcaccagt       1151
tgcagagaaa tcagcaagca cctag                                             1176

<210> SEQ ID NO 8
<211> LENGTH: 296
<212> TYPE: PRT
<213> ORGANISM: Homo sapiens

<400> SEQUENCE: 8

Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
    50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Val Lys Glu Thr His Leu
                260                 265                 270
```

```
Gln Met Arg Leu Trp Thr Trp Asp Phe Arg Val Asn Ala Leu Glu Asp
            275                 280                 285

Tyr Cys Glu Gly Leu Thr Val Phe
            290                 295

<210> SEQ ID NO 9
<211> LENGTH: 1221
<212> TYPE: DNA
<213> ORGANISM: Homo sapiens
<220> FEATURE:
<221> NAME/KEY: CDS
<222> LOCATION: (1)...(804)

<400> SEQUENCE: 9 atg tcc atg aac aat tcc aaa cag cta gtg tct cct gca gct gcg ctt      48
Met Ser Met Asn Asn Ser Lys Gln Leu Val Ser Pro Ala Ala Ala Leu
 1               5                  10                  15 ctt tca aac aca acc tgc cag acg gaa aac cgg ctt tcc gta ttt ttt      96
Leu Ser Asn Thr Thr Cys Gln Thr Glu Asn Arg Leu Ser Val Phe Phe
             20                  25                  30 tca gta atc ttc atg aca gtg gga atc ttg tca aac agc ctt gcc atc     144
Ser Val Ile Phe Met Thr Val Gly Ile Leu Ser Asn Ser Leu Ala Ile
         35                  40                  45 gcc att ctc atg aag gca tat cag aga ttt aga cag aag tcc aag gca     192
Ala Ile Leu Met Lys Ala Tyr Gln Arg Phe Arg Gln Lys Ser Lys Ala
     50                  55                  60 tcg ttt ctg ctt ttg gcc agc ggc ctg gta atc act gat ttc ttt ggc     240
Ser Phe Leu Leu Leu Ala Ser Gly Leu Val Ile Thr Asp Phe Phe Gly
 65                  70                  75                  80 cat ctc atc aat gga gcc ata gca gta ttt gta tat gct tct gat aaa     288
His Leu Ile Asn Gly Ala Ile Ala Val Phe Val Tyr Ala Ser Asp Lys
                 85                  90                  95 gaa tgg atc cgc ttt gac caa tca aat gtc ctt tgc agt att ttt ggt     336
Glu Trp Ile Arg Phe Asp Gln Ser Asn Val Leu Cys Ser Ile Phe Gly
            100                 105                 110 atc tgc atg gtg ttt tct ggt ctg tgc cca ctt ctt cta ggc agt gtg     384
Ile Cys Met Val Phe Ser Gly Leu Cys Pro Leu Leu Leu Gly Ser Val
        115                 120                 125 atg gcc att gag cgg tgt att gga gtc aca aaa cca ata ttt cat tct     432
Met Ala Ile Glu Arg Cys Ile Gly Val Thr Lys Pro Ile Phe His Ser
    130                 135                 140 acg aaa att aca tcc aaa cat gtg aaa atg atg tta agt ggt gtg tgc     480
Thr Lys Ile Thr Ser Lys His Val Lys Met Met Leu Ser Gly Val Cys
145                 150                 155                 160 ttg ttt gct gtt ttc ata gct ttg ctg ccc atc ctt gga cat cga gac     528
Leu Phe Ala Val Phe Ile Ala Leu Leu Pro Ile Leu Gly His Arg Asp
                165                 170                 175 tat aaa att cag gcg tcg agg acc tgg tgt ttc tac aac aca gaa gac     576
Tyr Lys Ile Gln Ala Ser Arg Thr Trp Cys Phe Tyr Asn Thr Glu Asp
            180                 185                 190 atc aaa gac tgg gaa gat aga ttt tat ctt cta ctt ttt tct ttt ctg     624
Ile Lys Asp Trp Glu Asp Arg Phe Tyr Leu Leu Leu Phe Ser Phe Leu
        195                 200                 205 ggg ctc tta gcc ctt ggt gtt tca ttg ttg tgc aat gca atc aca gga     672
Gly Leu Leu Ala Leu Gly Val Ser Leu Leu Cys Asn Ala Ile Thr Gly
    210                 215                 220 att aca ctt tta aga gtt aaa ttt aaa agt cag cag cac aga caa ggc     720
Ile Thr Leu Leu Arg Val Lys Phe Lys Ser Gln Gln His Arg Gln Gly
225                 230                 235                 240 aga tct cat cat ttg gaa atg gta atc cag ctc ctg gcg ata atg tgt     768
```

```
Arg Ser His His Leu Glu Met Val Ile Gln Leu Leu Ala Ile Met Cys
            245                 250                 255 gtc tcc tgt att tgt tgg agc cca ttt ctg cga taa gacactcaac          814
Val Ser Cys Ile Cys Trp Ser Pro Phe Leu Arg  *
            260                 265 gagaaatgac agaaaaacaa ggtgtggatg gagaggcaac atgaaagtgg atcaaacaac   874
ttatacatgg gtgctggctc agacgtgaca cctgaggctc cagaactgga agtttatgcc   934
gtcaagttac aatggccaac attggaataa atggaaatca ttctctggaa acctgtgaaa   994
caacactttt tgctctccga atggcaacat ggaatcaaat cttagatcct tgggtatata  1054
ttcttctacg aaaggctgtc cttaagaatc tctataagct tgccagtcaa tgctgtggag  1114
tgcatgtcat cagcttacat atttgggagc ttagttccat taaaaattcc ttaaaggttg  1174
ctgctatttc tgagtcacca gttgcagaga aatcagcaag caccctag               1221

<210> SEQ ID NO 10
<211> LENGTH: 267
<212> TYPE: PRT
<213> ORGANISM: Homo sapiens

<400> SEQUENCE: 10

Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Arg
            260                 265
```

<210> SEQ ID NO 11
<211> LENGTH: 1328
<212> TYPE: DNA
<213> ORGANISM: Homo sapiens
<220> FEATURE:
<221> NAME/KEY: CDS
<222> LOCATION: (1)...(825)

<400> SEQUENCE: 11

| | | | | | | | | | | | | | | | | |
|---|---|---|---|---|---|---|---|---|---|---|---|---|---|---|---|---|
| atg | tcc | atg | aac | aat | tcc | aaa | cag | cta | gtg | tct | cct | gca | gct | gcg | ctt | 48 |
| Met | Ser | Met | Asn | Asn | Ser | Lys | Gln | Leu | Val | Ser | Pro | Ala | Ala | Ala | Leu | |
| 1 | | | | 5 | | | | | 10 | | | | | 15 | | |
| ctt | tca | aac | aca | acc | tgc | cag | acg | gaa | aac | cgg | ctt | tcc | gta | ttt | ttt | 96 |
| Leu | Ser | Asn | Thr | Thr | Cys | Gln | Thr | Glu | Asn | Arg | Leu | Ser | Val | Phe | Phe | |
| | | | 20 | | | | | 25 | | | | | 30 | | | |
| tca | gta | atc | ttc | atg | aca | gtg | gga | atc | ttg | tca | aac | agc | ctt | gcc | atc | 144 |
| Ser | Val | Ile | Phe | Met | Thr | Val | Gly | Ile | Leu | Ser | Asn | Ser | Leu | Ala | Ile | |
| | | 35 | | | | | 40 | | | | | 45 | | | | |
| gcc | att | ctc | atg | aag | gca | tat | cag | aga | ttt | aga | cag | aag | tcc | aag | gca | 192 |
| Ala | Ile | Leu | Met | Lys | Ala | Tyr | Gln | Arg | Phe | Arg | Gln | Lys | Ser | Lys | Ala | |
| | 50 | | | | | 55 | | | | | 60 | | | | | |
| tcg | ttt | ctg | ctt | ttg | gcc | agc | ggc | ctg | gta | atc | act | gat | ttc | ttt | ggc | 240 |
| Ser | Phe | Leu | Leu | Leu | Ala | Ser | Gly | Leu | Val | Ile | Thr | Asp | Phe | Phe | Gly | |
| 65 | | | | | 70 | | | | | 75 | | | | | 80 | |
| cat | ctc | atc | aat | gga | gcc | ata | gca | gta | ttt | gta | tat | gct | tct | gat | aaa | 288 |
| His | Leu | Ile | Asn | Gly | Ala | Ile | Ala | Val | Phe | Val | Tyr | Ala | Ser | Asp | Lys | |
| | | | | 85 | | | | | 90 | | | | | 95 | | |
| gaa | tgg | atc | cgc | ttt | gac | caa | tca | aat | gtc | ctt | tgc | agt | att | ttt | ggt | 336 |
| Glu | Trp | Ile | Arg | Phe | Asp | Gln | Ser | Asn | Val | Leu | Cys | Ser | Ile | Phe | Gly | |
| | | | 100 | | | | | 105 | | | | | 110 | | | |
| atc | tgc | atg | gtg | ttt | tct | ggt | ctg | tgc | cca | ctt | ctt | cta | ggc | agt | gtg | 384 |
| Ile | Cys | Met | Val | Phe | Ser | Gly | Leu | Cys | Pro | Leu | Leu | Leu | Gly | Ser | Val | |
| | | 115 | | | | | 120 | | | | | 125 | | | | |
| atg | gcc | att | gag | cgg | tgt | att | gga | gtc | aca | aaa | cca | ata | ttt | cat | tct | 432 |
| Met | Ala | Ile | Glu | Arg | Cys | Ile | Gly | Val | Thr | Lys | Pro | Ile | Phe | His | Ser | |
| | 130 | | | | | 135 | | | | | 140 | | | | | |
| acg | aaa | att | aca | tcc | aaa | cat | gtg | aaa | atg | atg | tta | agt | ggt | gtg | tgc | 480 |
| Thr | Lys | Ile | Thr | Ser | Lys | His | Val | Lys | Met | Met | Leu | Ser | Gly | Val | Cys | |
| 145 | | | | | 150 | | | | | 155 | | | | | 160 | |
| ttg | ttt | gct | gtt | ttc | ata | gct | ttg | ctg | ccc | atc | ctt | gga | cat | cga | gac | 528 |
| Leu | Phe | Ala | Val | Phe | Ile | Ala | Leu | Leu | Pro | Ile | Leu | Gly | His | Arg | Asp | |
| | | | | 165 | | | | | 170 | | | | | 175 | | |
| tat | aaa | att | cag | gcg | tcg | agg | acc | tgg | tgt | ttc | tac | aac | aca | gaa | gac | 576 |
| Tyr | Lys | Ile | Gln | Ala | Ser | Arg | Thr | Trp | Cys | Phe | Tyr | Asn | Thr | Glu | Asp | |
| | | | 180 | | | | | 185 | | | | | 190 | | | |
| atc | aaa | gac | tgg | gaa | gat | aga | ttt | tat | ctt | cta | ctt | ttt | tct | ttt | ctg | 624 |
| Ile | Lys | Asp | Trp | Glu | Asp | Arg | Phe | Tyr | Leu | Leu | Leu | Phe | Ser | Phe | Leu | |
| | | 195 | | | | | 200 | | | | | 205 | | | | |
| ggg | ctc | tta | gcc | ctt | ggt | gtt | tca | ttg | tgc | aat | gca | atc | aca | gga | | 672 |
| Gly | Leu | Leu | Ala | Leu | Gly | Val | Ser | Leu | Leu | Cys | Asn | Ala | Ile | Thr | Gly | |
| | 210 | | | | | 215 | | | | | 220 | | | | | |
| att | aca | ctt | tta | aga | gtt | aaa | ttt | aaa | agt | cag | cag | cac | aga | caa | ggc | 720 |
| Ile | Thr | Leu | Leu | Arg | Val | Lys | Phe | Lys | Ser | Gln | Gln | His | Arg | Gln | Gly | |
| 225 | | | | | 230 | | | | | 235 | | | | | 240 | |
| aga | tct | cat | cat | ttg | gaa | atg | gta | atc | cag | ctc | ctg | gcg | ata | atg | tgt | 768 |
| Arg | Ser | His | His | Leu | Glu | Met | Val | Ile | Gln | Leu | Leu | Ala | Ile | Met | Cys | |
| | | | | 245 | | | | | 250 | | | | | 255 | | |
| gtc | tcc | tgt | att | tgt | tgg | agc | cca | ttt | ctg | aca | cat | tgg | ggt | aaa | gaa | 816 |
| Val | Ser | Cys | Ile | Cys | Trp | Ser | Pro | Phe | Leu | Thr | His | Trp | Gly | Lys | Glu | |
| | | | | 260 | | | | | 265 | | | | | 270 | | |

```
att cca tga tccctcctgt gcctaagcca ccccagtgga cctggtcttc      865
Ile Pro  * ttgcaccatc cctgtggctg gaggtttgag atactgacag cgataagaca ctcaacgaga  925
aatgacagaa aaacaaggtg tggatggaga ggcaacatga aagtggatca acaacttat   985 acatgggtgc tggctcagac gtgacacctg aggctccaga actggaagtt tatgccgtca  1045
agttacaatg gccaacattg gaataaatgg aaatcattct ctggaaacct gtgaaacaac  1105 acttttgct ctccgaatgg caacatggaa tcaaatctta gatccttggg tatatattct    1165
tctacgaaag gctgtcctta agaatctcta taagcttgcc agtcaatgct gtggagtgca  1225
tgtcatcagc ttacatattt gggagcttag ttccattaaa aattccttaa aggttgctgc  1285
tatttctgag tcaccagttg cagagaaatc agcaagcacc tag                    1328
```

<210> SEQ ID NO 12
<211> LENGTH: 274
<212> TYPE: PRT
<213> ORGANISM: Homo sapiens

<400> SEQUENCE: 12

```
Met Ser Met Asn Asn Ser Lys Gln Leu Val Ser Pro Ala Ala Ala Leu
 1               5                  10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
    50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Thr His Trp Gly Lys Glu
            260                 265                 270
```

Ile Pro

```
<210> SEQ ID NO 13
<211> LENGTH: 3095
<212> TYPE: DNA
<213> ORGANISM: Homo sapiens
<220> FEATURE:
<221> NAME/KEY: CDS
<222> LOCATION: (152)...(1228)

<400> SEQUENCE: 13
```

| | | |
|---|---|---|
| ggcgcgggc gccatggcac accgagcggc tccgtcttct gctcctcaga gagcccggct | 60 |
| ggcggcctgg gatgacaaga tgtctggact gcaatcctgc acagttttga gagggagatg | 120 |
| acttgagtgg ttggctttta tctccacaac a atg tcc atg aac aat tcc aaa | 172 |
|                                               Met Ser Met Asn Asn Ser Lys | |
|                                                 1            5 | |

```
cag cta gtg tct cct gca gct gcg ctt ctt tca aac aca acc tgc cag      220
Gln Leu Val Ser Pro Ala Ala Ala Leu Leu Ser Asn Thr Thr Cys Gln
         10                  15                  20 acg gaa aac cgg ctt tcc gta ttt ttt tca gta atc ttc atg aca gtg      268
Thr Glu Asn Arg Leu Ser Val Phe Phe Ser Val Ile Phe Met Thr Val
 25                  30                  35 gga atc ttg tca aac agc ctt gcc atc gcc att ctc atg aag gca tat      316
Gly Ile Leu Ser Asn Ser Leu Ala Ile Ala Ile Leu Met Lys Ala Tyr
 40                  45                  50                  55 cag aga ttt aga cag aag tcc aag gca tcg ttt ctg ctt ttg gcc agc      364
Gln Arg Phe Arg Gln Lys Ser Lys Ala Ser Phe Leu Leu Leu Ala Ser
             60                  65                  70 ggc ctg gta atc act gat ttc ttt ggc cat ctc atc aat gga gcc ata      412
Gly Leu Val Ile Thr Asp Phe Phe Gly His Leu Ile Asn Gly Ala Ile
         75                  80                  85 gca gta ttt gta tat gct tct gat aaa gaa tgg atc cgc ttt gac caa      460
Ala Val Phe Val Tyr Ala Ser Asp Lys Glu Trp Ile Arg Phe Asp Gln
         90                  95                 100 tca aat gtc ctt tgc agt att ttt ggt atc tgc atg gtg ttt tct ggt      508
Ser Asn Val Leu Cys Ser Ile Phe Gly Ile Cys Met Val Phe Ser Gly
105                 110                 115 ctg tgc cca ctt ctt cta ggc agt gtg atg gcc att gag cgg tgt att      556
Leu Cys Pro Leu Leu Leu Gly Ser Val Met Ala Ile Glu Arg Cys Ile
120                 125                 130                 135 gga gtc aca aaa cca ata ttt cat tct acg aaa att aca tcc aaa cat      604
Gly Val Thr Lys Pro Ile Phe His Ser Thr Lys Ile Thr Ser Lys His
             140                 145                 150 gtg aaa atg atg tta agt ggt gtg tgc ttg ttt gct gtt ttc ata gct      652
Val Lys Met Met Leu Ser Gly Val Cys Leu Phe Ala Val Phe Ile Ala
         155                 160                 165 ttg ctg ccc atc ctt gga cat cga gac tat aaa att cag gcg tcg agg      700
Leu Leu Pro Ile Leu Gly His Arg Asp Tyr Lys Ile Gln Ala Ser Arg
         170                 175                 180 acc tgg tgt ttc tac aac aca gaa gac atc aaa gac tgg gaa gat aga      748
Thr Trp Cys Phe Tyr Asn Thr Glu Asp Ile Lys Asp Trp Glu Asp Arg
     185                 190                 195 ttt tat ctt cta ctt ttt tct ttt ctg ggg ctc tta gcc ctt ggt gtt      796
Phe Tyr Leu Leu Leu Phe Ser Phe Leu Gly Leu Leu Ala Leu Gly Val
200                 205                 210                 215 tca ttg ttg tgc aat gca atc aca gga att aca ctt tta aga gtt aaa      844
Ser Leu Leu Cys Asn Ala Ile Thr Gly Ile Thr Leu Leu Arg Val Lys
                 220                 225                 230 ttt aaa agt cag cag cac aga caa ggc aga tct cat cat ttg gaa atg      892
Phe Lys Ser Gln Gln His Arg Gln Gly Arg Ser His His Leu Glu Met
```

-continued

```
                 235                 240                 245
gta atc cag ctc ctg gcg ata atg tgt gtc tcc tgt att tgt tgg agc       940
Val Ile Gln Leu Leu Ala Ile Met Cys Val Ser Cys Ile Cys Trp Ser
            250                 255                 260 cca ttt ctg gtt aca atg gcc aac att gga ata aat gga aat cat tct       988
Pro Phe Leu Val Thr Met Ala Asn Ile Gly Ile Asn Gly Asn His Ser
    265                 270                 275 ctg gaa acc tgt gaa aca aca ctt ttt gct ctc cga atg gca aca tgg      1036
Leu Glu Thr Cys Glu Thr Thr Leu Phe Ala Leu Arg Met Ala Thr Trp
280                 285                 290                 295 aat caa atc tta gat cct tgg gta tat att ctt cta cga aag gct gtc      1084
Asn Gln Ile Leu Asp Pro Trp Val Tyr Ile Leu Leu Arg Lys Ala Val
                300                 305                 310 ctt aag aat ctc tat aag ctt gcc agt caa tgc tgt gga gtg cat gtc      1132
Leu Lys Asn Leu Tyr Lys Leu Ala Ser Gln Cys Cys Gly Val His Val
            315                 320                 325 atc agc tta cat att tgg gag ctt agt tcc att aaa aat tcc tta aag      1180
Ile Ser Leu His Ile Trp Glu Leu Ser Ser Ile Lys Asn Ser Leu Lys
        330                 335                 340 gtt gct gct att tct gag tca cca gtt gca gag aaa tca gca agc acc      1228
Val Ala Ala Ile Ser Glu Ser Pro Val Ala Glu Lys Ser Ala Ser Thr
    345                 350                 355 tagcttaata ggacagtaaa tctgtgtggg gctagaacaa aaattaagac atgtttggca    1288
atatttcagt tagttaaata cctgtagcct aactggaaaa ttcaggcttc atcatgtagt    1348
ttgaagatac tattgtcaga ttcaggtttt gaaatttgtc aaataaacag ataactgta    1408
cattttcaac ttgttttttgc caatgggagg tagacacaat aaaataatgc catgggagtc   1468
acactgaaag caattttgag cttatctgtc ttatttatgc tttgagtgaa tcatctgttg    1528
aggtctaatg cctctacttg gcctatttgc cagagaacat cttaatgcag cctgcatagt    1588
gaaatggtta ttttgagatc accgctctgt agctaaccct tataaactag gctcagtaaa    1648
ataaagcact cttattttttt gatctggcct attttgcccc tcattgtgta gcctcaatta    1708
acacatgcat ggtcatgaca cccagaattc atgatggttt gttataacaa cctctgcata    1768
ttccaggtct ggcagacagg ttgcctgacc ctgcaatcct atctagaatg ggcccattct    1828
tgtcacattt gacaaatagg actgcctaca tttattatta tgaaggtcga ttgttgttgg    1888
aagtgttttt tcatgtcata gattagcaat tttcaaataa ttatttttc tctgaaaatt    1948
ttgtgtgtga ttgcacaata aataattttt agagaaacaa aggctctttc tcagcacatt    2008
gatgggcaac tagaattaca gcagtttcaa actctaccat ggataatgca aacaaaccga    2068
agctacatgc caatgatagg tgcaaagaat attggcaaaa ggtgctttac cttgagccat    2128
tatttgtgtc agagaacaaa agaaacagaa tcaatatata aattcaaaga ctatctgcag    2188
ctagtgtgtt tcttctttac acacatatac acacagacat cagaaaattc tgttgagagc    2248
aggttcatta aatttgtaag atggcatatt ctaaagcctg tgctaccagt actaagaggg    2308
gaagactggc aatttgccaa gcacttgggg attattataa caattaacta ggagatcaag    2368
agataataat ctctccccaa attttccaat aataattgag acttttttctt tgcttgtttg    2428
tgtaattcaa ccaaaagaat ttcaataccc attcaaattg tcctaggtct atcagaaatt    2488
agggaaggta gtcctgcttt ataataggaa aatgtatttc tgtataagat ttctttgctt    2548
tcattaaaaa tgggattcat ttaaaaatta atctttccct gttaggctga tttcagattc    2608
tctaggaaat ctggtgaagt aaccagaaga ctttcagatg gtttatttgc tttcagcaga    2668
gaatttattt catacagtta cttaagagtg ttgatgtctt gtgaacagag atataaggaa    2728
```

-continued

```
ccattctcca tccttcctta tcatgctggg tacaatgctt ctatgaatat ttccatgtat    2788
tttgactggg gagaggcatg gagaagaaac tctcattcag gggctccagg atccttctcc    2848
ttgaggcttc taaataaatg gcagaattct tgctgtattg ccatgatgtc accctggcca    2908
tgtgtactga cttgaggaga tcttgcaaca tggccatgtg caaggcttta aggagtgaga    2968
gagatgtgta catatcttag gagggttatc tatgttatct gagtatatgt ttgggtaacc    3028
aaattggtct taaaaatgat gttaacccaa gaagtagaca tcaaaaatta aaaaaaaaa     3088 aaaaaaa                                                              3095
```

<210> SEQ ID NO 14
<211> LENGTH: 359
<212> TYPE: PRT
<213> ORGANISM: Homo sapiens

<400> SEQUENCE: 14

```
Met Ser Met Asn Asn Ser Lys Gln Leu Val Ser Pro Ala Ala Ala Leu
 1               5                   10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala
    50                  55                  60

Ser Phe Leu Leu Leu Ala Ser Gly Leu Val Ile Thr Asp Phe Phe Gly
65                  70                  75                  80

His Leu Ile Asn Gly Ala Ile Ala Val Phe Val Tyr Ala Ser Asp Lys
                85                  90                  95

Glu Trp Ile Arg Phe Asp Gln Ser Asn Val Leu Cys Ser Ile Phe Gly
            100                 105                 110

Ile Cys Met Val Phe Ser Gly Leu Cys Pro Leu Leu Leu Gly Ser Val
        115                 120                 125

Met Ala Ile Glu Arg Cys Ile Gly Val Thr Lys Pro Ile Phe His Ser
    130                 135                 140

Thr Lys Ile Thr Ser Lys His Val Lys Met Met Leu Ser Gly Val Cys
145                 150                 155                 160

Leu Phe Ala Val Phe Ile Ala Leu Leu Pro Ile Leu Gly His Arg Asp
                165                 170                 175

Tyr Lys Ile Gln Ala Ser Arg Thr Trp Cys Phe Tyr Asn Thr Glu Asp
            180                 185                 190

Ile Lys Asp Trp Glu Asp Arg Phe Tyr Leu Leu Leu Phe Ser Phe Leu
        195                 200                 205

Gly Leu Leu Ala Leu Gly Val Ser Leu Leu Cys Asn Ala Ile Thr Gly
    210                 215                 220

Ile Thr Leu Leu Arg Val Lys Phe Lys Ser Gln Gln His Arg Gln Gly
225                 230                 235                 240

Arg Ser His His Leu Glu Met Val Ile Gln Leu Leu Ala Ile Met Cys
                245                 250                 255

Val Ser Cys Ile Cys Trp Ser Pro Phe Leu Val Thr Met Ala Asn Ile
            260                 265                 270

Gly Ile Asn Gly Asn His Ser Leu Glu Thr Cys Glu Thr Thr Leu Phe
        275                 280                 285

Ala Leu Arg Met Ala Thr Trp Asn Gln Ile Leu Asp Pro Trp Val Tyr
    290                 295                 300
```

-continued

```
Ile Leu Leu Arg Lys Ala Val Leu Lys Asn Leu Tyr Lys Leu Ala Ser
305                 310                 315                 320

Gln Cys Cys Gly Val His Val Ile Ser Leu His Ile Trp Glu Leu Ser
                325                 330                 335

Ser Ile Lys Asn Ser Leu Lys Val Ala Ala Ile Ser Glu Ser Pro Val
            340                 345                 350

Ala Glu Lys Ser Ala Ser Thr
            355
```

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tgcaatgcaa tcacaggaat                                           20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cactccacag cattgactgg                                           20

<210> SEQ ID NO 17
<211> LENGTH: 9
<212> TYPE: PRT
<213> ORGANISM: Homo sapiens

<400> SEQUENCE: 17

```
Ser Pro Phe Leu Gly Tyr Arg Ile Ile
1               5
```

<210> SEQ ID NO 18
<211> LENGTH: 9
<212> TYPE: PRT
<213> ORGANISM: Homo sapiens

<400> SEQUENCE: 18

```
Ser Pro Phe Leu Lys Ile Glu Gly Lys
1               5
```

<210> SEQ ID NO 19
<211> LENGTH: 9
<212> TYPE: PRT
<213> ORGANISM: Homo sapiens

<400> SEQUENCE: 19

```
Ser Pro Phe Leu Val Lys Glu Thr His
1               5
```

<210> SEQ ID NO 20
<211> LENGTH: 9
<212> TYPE: PRT
<213> ORGANISM: Homo sapiens

<400> SEQUENCE: 20

```
Ser Pro Phe Leu Thr His Trp Gly Lys
```

<210> SEQ ID NO 21
<211> LENGTH: 31
<212> TYPE: PRT
<213> ORGANISM: Homo sapiens

<400> SEQUENCE: 21

Gly Tyr Arg Ile Ile Leu Asn Gly Lys Glu Lys Tyr Lys Val Tyr Glu
 1               5                  10                  15

Glu Gln Ser Asp Phe Leu His Arg Leu Gln Trp Pro Thr Leu Glu
            20                  25                  30

<210> SEQ ID NO 22
<211> LENGTH: 9
<212> TYPE: PRT
<213> ORGANISM: Homo sapiens

<400> SEQUENCE: 22

Lys Ile Glu Gly Lys Ile Lys Val Thr
 1               5

<210> SEQ ID NO 23
<211> LENGTH: 25
<212> TYPE: PRT
<213> ORGANISM: Homo sapiens

<400> SEQUENCE: 23

Gly Tyr Arg Ile Ile Leu Asn Gly Lys Glu Lys Tyr Lys Val Tyr Glu
 1               5                  10                  15

Glu Gln Ser Asp Phe Leu His Arg Lys
            20                  25

<210> SEQ ID NO 24
<211> LENGTH: 30
<212> TYPE: PRT
<213> ORGANISM: Homo sapiens

<400> SEQUENCE: 24

Val Lys Glu Thr His Leu Gln Met Arg Leu Trp Thr Trp Asp Phe Arg
 1               5                  10                  15

Val Asn Ala Leu Glu Asp Tyr Cys Glu Gly Leu Thr Val Phe
            20                  25                  30

<210> SEQ ID NO 25
<211> LENGTH: 8
<212> TYPE: PRT
<213> ORGANISM: Homo sapiens

<400> SEQUENCE: 25

Thr His Trp Gly Lys Glu Ile Pro
 1               5

<210> SEQ ID NO 26
<211> LENGTH: 20
<212> TYPE: DNA
<213> ORGANISM: Homo sapiens

<400> SEQUENCE: 26
ccatttctgg gatacagaat                                        20

<210> SEQ ID NO 27
<211> LENGTH: 20

<212> TYPE: DNA
<213> ORGANISM: Homo sapiens

<400> SEQUENCE: 27
cttacatagg ttacaatggc 20

<210> SEQ ID NO 28
<211> LENGTH: 20
<212> TYPE: DNA
<213> ORGANISM: Homo sapiens

<400> SEQUENCE: 28
cccatttctg aaaatagaag 20

<210> SEQ ID NO 29
<211> LENGTH: 20
<212> TYPE: DNA
<213> ORGANISM: Homo sapiens

<400> SEQUENCE: 29
tgttggaaag gttacaatgg 20

<210> SEQ ID NO 30
<211> LENGTH: 20
<212> TYPE: DNA
<213> ORGANISM: Homo sapiens

<400> SEQUENCE: 30
ccatttctgg tgaaagaaac 20

<210> SEQ ID NO 31
<211> LENGTH: 20
<212> TYPE: DNA
<213> ORGANISM: Homo sapiens

<400> SEQUENCE: 31
ttttgaaatg ttacaatggc 20

<210> SEQ ID NO 32
<211> LENGTH: 20
<212> TYPE: DNA
<213> ORGANISM: Homo sapiens

<400> SEQUENCE: 32
cccatttctg cgataagaca 20

<210> SEQ ID NO 33
<211> LENGTH: 20
<212> TYPE: DNA
<213> ORGANISM: Homo sapiens

<400> SEQUENCE: 33
atgccgtcaa gttacaatgg 20

<210> SEQ ID NO 34
<211> LENGTH: 20
<212> TYPE: DNA
<213> ORGANISM: Homo sapiens

<400> SEQUENCE: 34
cccatttctg acacattggg 20

<210> SEQ ID NO 35

```
<211> LENGTH: 20
<212> TYPE: DNA
<213> ORGANISM: Artificial Sequence
<220> FEATURE:
<223> OTHER INFORMATION: primer

<400> SEQUENCE: 35
gagcccattt ctgggataca                                               20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
agtgcctctc ttcaccctca                                               20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
agcccatttc tgcgataaga                                               20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gttctggagc ctcaggtgtc                                               20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
agctcctggc gataatgtgt                                               20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ccyychcaay ahyccyccaa                                               20
```